(12) United States Patent
Gonzalez et al.

(10) Patent No.: US 11,124,751 B2
(45) Date of Patent: Sep. 21, 2021

(54) SUPPLYING TREATED EXHAUST GASES FOR EFFECTING GROWTH OF PHOTOTROPHIC BIOMASS

(71) Applicant: POND TECHNOLOGIES INC., Markham (CA)

(72) Inventors: Jaime A. Gonzalez, Markham (CA); Max Kolesnik, Toronto (CA); Steven C. Martin, Toronto (CA)

(73) Assignee: Pond Technologies Inc., Markham (CA)

( * ) Notice: Subject to any disclaimer, the term of this patent is extended or adjusted under 35 U.S.C. 154(b) by 113 days.

(21) Appl. No.: 14/991,563

(22) Filed: Jan. 8, 2016

(65) Prior Publication Data
US 2016/0115439 A1  Apr. 28, 2016

Related U.S. Application Data

(63) Continuation of application No. 13/095,490, filed on Apr. 27, 2011, now abandoned.

(51) Int. Cl.
| | |
|---|---|
| *C12N 1/12* | (2006.01) |
| *C12M 1/00* | (2006.01) |
| *C12M 1/04* | (2006.01) |
| *A01G 33/00* | (2006.01) |
| *C07K 14/47* | (2006.01) |
| *C12M 1/34* | (2006.01) |
| *C12N 5/04* | (2006.01) |

(52) U.S. Cl.
CPC ............ *C12M 21/02* (2013.01); *A01G 33/00* (2013.01); *C07K 14/472* (2013.01); *C12M 41/34* (2013.01); *C12M 43/04* (2013.01); *C12N 1/12* (2013.01); *C12N 5/04* (2013.01); *Y02C 20/40* (2020.08)

(58) Field of Classification Search
None
See application file for complete search history.

(56) References Cited

U.S. PATENT DOCUMENTS

| | | | |
|---|---|---|---|
| 2,658,310 A | 11/1953 | Cook | |
| 2,715,795 A | 8/1955 | Pallotta et al. | |
| 2,732,661 A | 1/1956 | Spoehr et al. | |
| 2,732,663 A | 1/1956 | Dewey, II | |
| 2,815,607 A | 12/1957 | Schroeder | |
| 2,854,792 A | 10/1958 | Walter | |
| 3,224,143 A | 12/1965 | Tew et al. | |
| 3,243,918 A | 4/1966 | Lauro | |
| 3,303,608 A | 2/1967 | Hannan | |
| 3,403,471 A | 10/1968 | Genevieve et al. | |
| 3,504,185 A | 3/1970 | Zweig et al. | |
| 3,650,068 A | 3/1972 | Meyer et al. | |
| 3,712,025 A | 1/1973 | Wallace | |
| 3,763,824 A | 10/1973 | Schoon | |
| 3,855,121 A | 12/1974 | Gough | |
| 3,882,635 A | 5/1975 | Yamanaka et al. | |
| 3,959,923 A | 6/1976 | Selke | |
| 3,986,297 A | 10/1976 | Ichimura et al. | |
| 4,043,903 A | 8/1977 | Dor | |
| 4,078,331 A | 3/1978 | Savins et al. | |
| 4,084,346 A | 4/1978 | Stengel et al. | |
| 4,087,936 A | 5/1978 | Savins et al. | |
| 4,116,778 A | 9/1978 | Belousov et al. | |
| 4,235,043 A | 11/1980 | Harasawa et al. | |
| 4,253,271 A | 3/1981 | Raymond | |
| 4,267,038 A | 5/1981 | Thompson | |
| 4,297,000 A | 10/1981 | Fries | |
| 4,324,068 A | 4/1982 | Anthony | |
| 4,341,038 A | 7/1982 | Bloch et al. | |
| 4,383,039 A | 5/1983 | Leavitt | |
| 4,398,926 A | 8/1983 | Doshi | |
| 4,417,415 A | 11/1983 | Cysewski et al. | |
| 4,438,591 A | 3/1984 | Kessler | |
| 4,442,211 A | 4/1984 | Greenbaum | |
| 4,473,970 A | 10/1984 | Hills | |

(Continued)

FOREIGN PATENT DOCUMENTS

| | | |
|---|---|---|
| CA | 2738516 | 4/2011 |
| CA | 2738397 A1 | 11/2011 |

(Continued)

OTHER PUBLICATIONS

Patent Examination Report No. 1, issued in corresponding Australian Patent Application No. 2012248080, dated Dec. 10, 2015.
Matthijs et al. "Application of light emitting diodes in bioreactors: flashing light effects and energy economy in algal culture." Biotechnol. Bioeng. [Online] 2000, 50, pp. 98-107.
Lee et al. "High density algal photobioreactors using light emitting diodes." Biotech. BioEng. [Online] 1994, 44. pp. 1161-1167.
Fernandez et al. "Airlift-driven external-loop tubular photobioreactors for outdoor production of microalgae assessment of design and performance" Chemical Engineering Science [Online], 2001, 56, 2721-2732.

(Continued)

*Primary Examiner* — Cynthia E Collins
(74) *Attorney, Agent, or Firm* — Ridout and Maybee LLP

(57) ABSTRACT

There is provided a process for growing a phototrophic biomass in a reaction zone. The process includes treating an operative carbon dioxide supply-comprising gaseous material feed so as to effect production of a carbon dioxide-rich product material. The carbon dioxide concentration of the carbon dioxide-rich product material is greater than the carbon dioxide concentration of the operative carbon dioxide supply-comprising gaseous material feed. Production of at least a fraction of the operative carbon dioxide supply-comprising gaseous material feed is effected by a gaseous exhaust material producing process. At least a fraction of the carbon dioxide-rich product material is supplied to the reaction zone so as to effect growth of the phototrophic biomass by photosynthesis in the reaction zone.

10 Claims, 2 Drawing Sheets

(56) References Cited

U.S. PATENT DOCUMENTS

| | | |
|---|---|---|
| 4,525,031 A | 6/1985 | Mori |
| 4,539,625 A | 9/1985 | Bornstein et al. |
| 4,595,405 A | 6/1986 | Agrawal et al. |
| 4,626,065 A | 12/1986 | Mori |
| 4,676,956 A | 6/1987 | Mori |
| 4,681,612 A | 7/1987 | O Brien et al. |
| 4,724,214 A | 2/1988 | Mori |
| 4,781,843 A | 11/1988 | Baker et al. |
| 4,851,339 A | 7/1989 | Hills |
| 4,865,969 A | 9/1989 | Amen et al. |
| 4,869,017 A | 9/1989 | Bird et al. |
| 4,889,812 A | 12/1989 | Guinn et al. |
| 4,900,678 A | 2/1990 | Mori |
| 4,939,087 A | 7/1990 | Van et al. |
| 4,952,511 A | 8/1990 | Radmer |
| 4,958,460 A | 9/1990 | Nielson et al. |
| 4,970,166 A | 11/1990 | Mori |
| 4,995,377 A | 2/1991 | Eiden |
| 5,040,486 A | 8/1991 | Pack |
| 5,081,036 A | 1/1992 | Familletti |
| 5,104,803 A | 4/1992 | Delente |
| 5,151,342 A | 9/1992 | Wiedemann |
| 5,151,347 A | 9/1992 | Delente et al. |
| 5,206,173 A | 4/1993 | Finn |
| 5,216,976 A | 6/1993 | Marinkovich |
| 5,330,915 A | 7/1994 | Wilson et al. |
| 5,334,497 A | 8/1994 | Inaba et al. |
| 5,358,858 A | 10/1994 | Chiang et al. |
| 5,424,209 A | 6/1995 | Kearney |
| 5,447,629 A | 9/1995 | Chaumont et al. |
| 5,534,404 A | 7/1996 | Laurance et al. |
| 5,534,417 A | 7/1996 | Arad et al. |
| 5,541,056 A | 7/1996 | Huntley et al. |
| 5,552,058 A | 9/1996 | Fanning |
| 5,558,984 A | 9/1996 | Young et al. |
| 5,565,108 A | 10/1996 | Dimesky et al. |
| 5,573,669 A | 11/1996 | Jensen |
| 5,578,472 A | 11/1996 | Ueda et al. |
| 5,614,378 A | 3/1997 | Yang et al. |
| 5,656,421 A | 8/1997 | Gebhard et al. |
| 5,659,977 A | 8/1997 | Jensen et al. |
| 5,670,046 A | 9/1997 | Kimmel |
| 5,682,709 A | 11/1997 | Erickson |
| 5,686,299 A | 11/1997 | Colwell et al. |
| 5,711,983 A | 1/1998 | Kyle et al. |
| 5,741,702 A | 4/1998 | Lorenz |
| 5,744,041 A | 4/1998 | Grove |
| 5,776,349 A | 7/1998 | Guelcher et al. |
| 5,843,762 A | 12/1998 | Moll |
| 5,846,435 A | 12/1998 | Haase |
| 5,846,816 A | 12/1998 | Forth |
| 5,851,398 A | 12/1998 | Adey |
| 5,871,952 A | 2/1999 | Ghirardi et al. |
| 5,882,849 A | 3/1999 | Leonard et al. |
| 5,897,997 A | 4/1999 | Louvel |
| 5,906,750 A | 5/1999 | Haase |
| 5,910,254 A | 6/1999 | Guelcher et al. |
| 5,912,113 A | 6/1999 | Nakamura et al. |
| 5,951,875 A | 9/1999 | Kanel et al. |
| 5,958,761 A | 9/1999 | Yogev et al. |
| 5,981,260 A | 11/1999 | Metz |
| 5,981,271 A | 11/1999 | Doucha et al. |
| 5,994,129 A | 11/1999 | Armstrong et al. |
| 6,000,551 A | 12/1999 | Kanel et al. |
| 6,022,701 A | 2/2000 | Boussiba et al. |
| 6,083,740 A | 7/2000 | Kodo et al. |
| 6,110,370 A | 8/2000 | Van et al. |
| 6,120,690 A | 9/2000 | Haase |
| 6,128,135 A | 10/2000 | Stiles et al. |
| 6,140,365 A | 10/2000 | Kiy et al. |
| 6,156,561 A | 12/2000 | Kodo et al. |
| 6,174,720 B1 | 1/2001 | Oxley et al. |
| 6,228,332 B1 | 5/2001 | Dunn et al. |
| 6,237,284 B1 | 5/2001 | Erickson |
| 6,258,588 B1 | 7/2001 | Demetropoulos et al. |
| 6,284,453 B1 | 9/2001 | Siano |
| 6,287,852 B1 | 9/2001 | Kondo et al. |
| 6,299,774 B1 | 10/2001 | Ainsworth et al. |
| 6,348,347 B1 | 2/2002 | Hirabayashi et al. |
| 6,391,238 B1 | 5/2002 | Sato et al. |
| 6,477,841 B1 | 11/2002 | Yantovsky |
| 6,492,149 B1 | 12/2002 | Muller |
| 6,509,188 B1 | 1/2003 | Trösch et al. |
| 6,524,486 B2 | 2/2003 | Borodyanski et al. |
| 6,571,735 B1 | 6/2003 | Wilkinson |
| 6,579,714 B1 | 6/2003 | Hirabayashi et al. |
| 6,602,703 B2 | 8/2003 | Dutil |
| 6,603,069 B1 | 8/2003 | Muhs et al. |
| 6,633,042 B1 | 10/2003 | Funken et al. |
| 6,648,949 B1 | 11/2003 | Der et al. |
| 6,667,171 B2 | 12/2003 | Bayless et al. |
| 6,673,532 B2 | 1/2004 | Rao |
| 6,673,592 B1 | 1/2004 | Wang et al. |
| 6,709,862 B2 | 3/2004 | Curtis |
| 6,792,336 B1 | 9/2004 | Johnson et al. |
| 6,815,204 B2 | 11/2004 | Muller et al. |
| 6,830,699 B2 | 12/2004 | Heidal et al. |
| 6,851,387 B2 | 2/2005 | Untermeyer et al. |
| 6,858,430 B1 | 2/2005 | Reddy et al. |
| 6,887,692 B2 | 5/2005 | Paterek |
| 6,918,354 B2 | 7/2005 | Perriello |
| 6,929,942 B2 | 8/2005 | Moghe et al. |
| 6,936,459 B1 | 8/2005 | Venkatesh et al. |
| 6,989,252 B2 | 1/2006 | Melis et al. |
| 6,991,919 B1 | 1/2006 | Porter et al. |
| 7,001,519 B2 | 2/2006 | Linden et al. |
| 7,022,232 B2 | 4/2006 | Jensen |
| 7,033,823 B2 | 4/2006 | Chang |
| 7,056,725 B1 | 6/2006 | Lu |
| 7,135,308 B1 | 11/2006 | Bush et al. |
| 7,135,332 B2 | 11/2006 | Ouellette |
| 7,153,344 B2 | 12/2006 | Filippi et al. |
| 7,163,811 B2 | 1/2007 | Behrens et al. |
| 7,172,691 B2 | 2/2007 | Dunlop et al. |
| 7,176,017 B2 | 2/2007 | Parent et al. |
| 7,176,024 B2 | 2/2007 | Branson et al. |
| 7,183,074 B2 | 2/2007 | Chen et al. |
| 7,191,597 B2 | 3/2007 | Goldman |
| 7,198,940 B2 | 4/2007 | Vellinger et al. |
| 7,252,979 B2 | 8/2007 | Behrens et al. |
| 7,270,996 B2 | 9/2007 | Cannon et al. |
| 7,279,314 B2 | 10/2007 | Matsuo |
| 7,320,889 B2 | 1/2008 | Kahlert et al. |
| 7,331,178 B2 | 2/2008 | Goldman |
| 7,333,195 B2 | 2/2008 | Kreiß et al. |
| 7,392,615 B2 | 7/2008 | Lee |
| 7,425,441 B2 | 9/2008 | Broneske et al. |
| 7,435,581 B2 | 10/2008 | West |
| 7,449,313 B2 | 11/2008 | Rush |
| 7,479,226 B2 | 1/2009 | Dunlop et al. |
| 7,507,554 B2 | 3/2009 | Bush et al. |
| 7,507,579 B2 | 3/2009 | Boccazzi et al. |
| 7,510,864 B2 | 3/2009 | Krichevsky et al. |
| 7,514,247 B2 | 4/2009 | Rush |
| 7,531,350 B2 | 5/2009 | Shiau |
| 7,536,827 B2 | 5/2009 | Busch et al. |
| 7,566,551 B2 | 7/2009 | Zhang |
| 7,572,546 B2 | 8/2009 | Karamanev |
| 7,585,898 B2 | 9/2009 | Thothathri |
| 7,618,813 B2 | 11/2009 | Lee et al. |
| 7,632,414 B2 | 12/2009 | Hsu |
| 7,635,586 B2 | 12/2009 | West |
| 7,658,851 B2 | 2/2010 | Nelson et al. |
| 7,662,615 B2 | 2/2010 | Chang et al. |
| 7,662,616 B2 | 2/2010 | Hazlebeck et al. |
| 7,662,617 B2 | 2/2010 | Rush |
| 7,682,821 B2 | 3/2010 | Woods et al. |
| 7,687,161 B2 | 3/2010 | Karamanev |
| 7,687,261 B2 | 3/2010 | Hazlebeck et al. |
| 7,736,508 B2 | 6/2010 | Limcaco |
| 7,750,494 B1 | 7/2010 | Behrens et al. |
| 7,770,322 B2 | 8/2010 | Huntley et al. |
| 7,771,515 B2 | 8/2010 | Champagne et al. |
| 7,905,049 B2 | 3/2011 | Erd |

(56) References Cited

U.S. PATENT DOCUMENTS

| | | |
|---|---|---|
| 7,977,085 B2 | 7/2011 | Rispoli et al. |
| 8,262,776 B2 * | 9/2012 | Hazlebeck ............. C12M 21/02 |
| | | 435/266 |
| 9,150,807 B2 * | 10/2015 | Sceats .................... B01D 53/62 |
| 2002/0034817 A1 | 3/2002 | Henry et al. |
| 2002/0072109 A1 | 6/2002 | Bayless et al. |
| 2002/0130076 A1 | 9/2002 | Merritt |
| 2002/0138454 A1 | 9/2002 | Gruenberg et al. |
| 2003/0044114 A1 | 3/2003 | Pelka |
| 2003/0153059 A1 | 8/2003 | Pilkington et al. |
| 2003/0155090 A1 | 8/2003 | Holmberg et al. |
| 2003/0162273 A1 | 8/2003 | Melis et al. |
| 2003/0228684 A1 | 12/2003 | Burbidge et al. |
| 2004/0077036 A1 | 4/2004 | Thomas et al. |
| 2004/0191755 A1 | 9/2004 | Kemper et al. |
| 2004/0266622 A1 | 12/2004 | Park |
| 2005/0036932 A1 | 2/2005 | Takahashi et al. |
| 2005/0037480 A1 | 2/2005 | Chiueh |
| 2005/0044911 A1 | 3/2005 | Shimose |
| 2005/0064577 A1 | 3/2005 | Berzin |
| 2005/0186671 A1 | 8/2005 | Cannon et al. |
| 2005/0239182 A1 | 10/2005 | Berzin |
| 2005/0244957 A1 | 11/2005 | Stock |
| 2005/0260553 A1 | 11/2005 | Berzin |
| 2006/0019375 A1 | 1/2006 | Seidl et al. |
| 2006/0134598 A1 | 6/2006 | Kenney |
| 2006/0151402 A1 | 7/2006 | Hsu |
| 2006/0216818 A1 | 9/2006 | Amano |
| 2006/0223155 A1 | 10/2006 | Streeter |
| 2006/0258000 A1 | 11/2006 | Allen et al. |
| 2006/0275858 A1 | 12/2006 | Saucedo et al. |
| 2006/0281163 A1 | 12/2006 | Diz et al. |
| 2007/0010002 A1 | 1/2007 | Melkonian et al. |
| 2007/0015263 A1 | 1/2007 | Wumpelmann |
| 2007/0042487 A1 | 2/2007 | Cheshire |
| 2007/0048848 A1 | 3/2007 | Sears |
| 2007/0048859 A1 | 3/2007 | Sears |
| 2007/0054351 A1 | 3/2007 | Zhang |
| 2007/0092962 A1 | 4/2007 | Sheppard |
| 2007/0113474 A1 | 5/2007 | Everett et al. |
| 2007/0114186 A1 | 5/2007 | Dart et al. |
| 2007/0157614 A1 | 7/2007 | Goldman |
| 2007/0161095 A1 | 7/2007 | Gurin |
| 2007/0202582 A1 | 8/2007 | Bush et al. |
| 2007/0264708 A1 | 11/2007 | Bayless et al. |
| 2007/0269874 A1 | 11/2007 | Kosourov et al. |
| 2007/0275856 A1 | 11/2007 | Thothathri |
| 2008/0009055 A1 | 1/2008 | Lewnard |
| 2008/0028675 A1 | 2/2008 | Clifford et al. |
| 2008/0044887 A1 | 2/2008 | Maltezos et al. |
| 2008/0050800 A1 | 2/2008 | McKeeman et al. |
| 2008/0052987 A1 | 3/2008 | Busch et al. |
| 2008/0085536 A1 | 4/2008 | Nobles et al. |
| 2008/0086938 A1 | 4/2008 | Hazlebeck et al. |
| 2008/0096267 A1 | 4/2008 | Howard et al. |
| 2008/0113413 A1 | 5/2008 | Nobles et al. |
| 2008/0115500 A1 | 5/2008 | MacAdam et al. |
| 2008/0118964 A1 | 5/2008 | Huntley et al. |
| 2008/0131958 A1 | 6/2008 | Remmereit et al. |
| 2008/0138875 A1 | 6/2008 | Atehortua et al. |
| 2008/0155890 A1 | 7/2008 | Oyler |
| 2008/0160591 A1 | 7/2008 | Willson et al. |
| 2008/0160593 A1 | 7/2008 | Oyler |
| 2008/0160597 A1 | 7/2008 | van et al. |
| 2008/0166779 A1 | 7/2008 | Thomas et al. |
| 2008/0176303 A1 | 7/2008 | Massie |
| 2008/0176304 A1 | 7/2008 | Lee |
| 2008/0178739 A1 | 7/2008 | Lewnard et al. |
| 2008/0182325 A1 | 7/2008 | Hobbs et al. |
| 2008/0210632 A1 | 9/2008 | Kruse |
| 2008/0213049 A1 | 9/2008 | Higgins et al. |
| 2008/0213868 A1 | 9/2008 | Fournier |
| 2008/0220486 A1 | 9/2008 | Weiss |
| 2008/0220489 A1 | 9/2008 | Offerman |
| 2008/0220515 A1 | 9/2008 | McCall |
| 2008/0241902 A1 | 10/2008 | Berry et al. |
| 2008/0254056 A1 | 10/2008 | Zhang |
| 2008/0268302 A1 | 10/2008 | McCall |
| 2008/0274494 A1 | 11/2008 | Kertz |
| 2008/0293132 A1 | 11/2008 | Goldman et al. |
| 2008/0299539 A1 | 12/2008 | Lee et al. |
| 2008/0299643 A1 | 12/2008 | Howard et al. |
| 2008/0303348 A1 | 12/2008 | Witters |
| 2008/0305539 A1 | 12/2008 | Hickey et al. |
| 2008/0311646 A1 | 12/2008 | Cong et al. |
| 2008/0318304 A1 | 12/2008 | Burton et al. |
| 2009/0004715 A1 | 1/2009 | Trimbur et al. |
| 2009/0011492 A1 | 1/2009 | Berzin |
| 2009/0017514 A1 | 1/2009 | Datta et al. |
| 2009/0023199 A1 | 1/2009 | Gal |
| 2009/0029445 A1 | 1/2009 | Eckelberry et al. |
| 2009/0035835 A1 | 2/2009 | Slavin |
| 2009/0047722 A1 * | 2/2009 | Wilkerson ............. C12M 21/02 |
| | | 435/173.7 |
| 2009/0047730 A1 | 2/2009 | Higgins et al. |
| 2009/0068715 A1 | 3/2009 | Ogaki et al. |
| 2009/0068727 A1 | 3/2009 | Karr |
| 2009/0075353 A1 | 3/2009 | Ogaki et al. |
| 2009/0077863 A1 | 3/2009 | Oyler |
| 2009/0077864 A1 | 3/2009 | Marker et al. |
| 2009/0081743 A1 | 3/2009 | Hazelbeck et al. |
| 2009/0081744 A1 | 3/2009 | Kastanek |
| 2009/0081748 A1 | 3/2009 | Oyler |
| 2009/0081770 A1 | 3/2009 | Srienc et al. |
| 2009/0087898 A1 * | 4/2009 | Haase ................... B01D 53/84 |
| | | 435/262.5 |
| 2009/0104594 A1 | 4/2009 | Webb |
| 2009/0113790 A1 | 5/2009 | Erd |
| 2009/0117647 A1 | 5/2009 | Buddhi et al. |
| 2009/0126265 A1 | 5/2009 | Rasmussen et al. |
| 2009/0130706 A1 | 5/2009 | Berzin et al. |
| 2009/0130747 A1 | 5/2009 | Wen-Teng et al. |
| 2009/0134091 A1 | 5/2009 | Stephens et al. |
| 2009/0137013 A1 | 5/2009 | Schmid et al. |
| 2009/0137025 A1 | 5/2009 | Stephens et al. |
| 2009/0148927 A1 | 6/2009 | Schroeder et al. |
| 2009/0148931 A1 | 6/2009 | Wilkerson et al. |
| 2009/0151240 A1 | 6/2009 | Kayama et al. |
| 2009/0151241 A1 | 6/2009 | Dressler et al. |
| 2009/0155864 A1 | 6/2009 | Bauer et al. |
| 2009/0170184 A1 | 7/2009 | Shepherd et al. |
| 2009/0181438 A1 | 7/2009 | Sayre |
| 2009/0197322 A1 | 8/2009 | Goldman |
| 2009/0203067 A1 | 8/2009 | Eckerle et al. |
| 2009/0203115 A1 | 8/2009 | Busch et al. |
| 2009/0203116 A1 | 8/2009 | Bazaire |
| 2009/0205638 A1 | 8/2009 | Corcoran |
| 2009/0215155 A1 | 8/2009 | Cloud et al. |
| 2009/0221057 A1 | 9/2009 | Kennedy |
| 2009/0227003 A1 | 9/2009 | Blotsky et al. |
| 2009/0227456 A1 | 9/2009 | Hsu |
| 2009/0230040 A1 | 9/2009 | Limcaco |
| 2009/0232861 A1 | 9/2009 | Wright et al. |
| 2009/0233334 A1 | 9/2009 | Hildinger et al. |
| 2009/0249685 A1 | 10/2009 | Flowers et al. |
| 2009/0250401 A1 | 10/2009 | Kotelko et al. |
| 2009/0263889 A1 | 10/2009 | Wumpelmann |
| 2009/0269839 A1 | 10/2009 | Oyler |
| 2009/0275120 A1 | 11/2009 | Koch et al. |
| 2009/0286295 A1 | 11/2009 | Medoff et al. |
| 2009/0286296 A1 | 11/2009 | Hickey et al. |
| 2009/0291485 A1 | 11/2009 | Shigematsu et al. |
| 2009/0294354 A1 | 12/2009 | Theodore et al. |
| 2009/0298159 A1 | 12/2009 | Wu et al. |
| 2009/0305388 A1 | 12/2009 | Dressler et al. |
| 2009/0309515 A1 | 12/2009 | Crabb et al. |
| 2009/0317901 A1 | 12/2009 | Vance |
| 2009/0321349 A1 | 12/2009 | Offerman et al. |
| 2009/0324799 A1 | 12/2009 | Hartman et al. |
| 2009/0325253 A1 | 12/2009 | Ascon et al. |
| 2010/0003717 A1 | 1/2010 | Oyler |
| 2010/0003741 A1 | 1/2010 | Fromson |
| 2010/0005711 A1 | 1/2010 | McNeff |
| 2010/0011778 A1 | 1/2010 | Knight et al. |

(56) References Cited

U.S. PATENT DOCUMENTS

| | | |
|---|---|---|
| 2010/0018214 A1 | 1/2010 | Halachmi |
| 2010/0021361 A1* | 1/2010 | Spencer .............. B01D 53/62 423/220 |
| 2010/0021968 A1 | 1/2010 | Hu et al. |
| 2010/0028976 A1 | 2/2010 | Hu et al. |
| 2010/0028977 A1 | 2/2010 | Ng et al. |
| 2010/0034050 A1 | 2/2010 | Erb et al. |
| 2010/0035321 A1 | 2/2010 | Wilkerson et al. |
| 2010/0035343 A1 | 2/2010 | Cheng et al. |
| 2010/0043446 A1 | 2/2010 | Shirvanian et al. |
| 2010/0050502 A1 | 3/2010 | Wu et al. |
| 2010/0055765 A1 | 3/2010 | Frank |
| 2010/0062483 A1 | 3/2010 | Beliaev et al. |
| 2010/0068693 A1 | 3/2010 | Tsang et al. |
| 2010/0068779 A1 | 3/2010 | Wells et al. |
| 2010/0068791 A1 | 3/2010 | Merimon et al. |
| 2010/0068801 A1 | 3/2010 | Woods et al. |
| 2010/0071370 A1 | 3/2010 | O Kane |
| 2010/0077654 A1 | 4/2010 | Wu et al. |
| 2010/0081122 A1 | 4/2010 | Shibuya et al. |
| 2010/0081177 A1 | 4/2010 | Schatz et al. |
| 2010/0081835 A1 | 4/2010 | Wu et al. |
| 2010/0093046 A1 | 4/2010 | Remmereit et al. |
| 2010/0093078 A1 | 4/2010 | Wang et al. |
| 2010/0099151 A1 | 4/2010 | Stroïazzo-Mougin et al. |
| 2010/0099157 A1 | 4/2010 | Salvetzki |
| 2010/0099170 A1 | 4/2010 | Aswani |
| 2010/0101621 A1 | 4/2010 | Xu |
| 2010/0105125 A1 | 4/2010 | Haley |
| 2010/0105126 A1 | 4/2010 | Wright et al. |
| 2010/0105127 A1 | 4/2010 | Ginsburg |
| 2010/0105129 A1 | 4/2010 | Sanchez-Pina et al. |
| 2010/0107487 A1 | 5/2010 | Holland |
| 2010/0112649 A1 | 5/2010 | Willson et al. |
| 2010/0112700 A1 | 5/2010 | Shaaltiel et al. |
| 2010/0120134 A1 | 5/2010 | Gal |
| 2010/0139265 A1 | 6/2010 | Stroïazzo |
| 2010/0151558 A1 | 6/2010 | Alianell et al. |
| 2010/0159539 A1 | 6/2010 | Ascon et al. |
| 2010/0159567 A1 | 6/2010 | Kuehnle et al. |
| 2010/0159578 A1 | 6/2010 | Lacaze et al. |
| 2010/0159579 A1 | 6/2010 | Schuring et al. |
| 2010/0162620 A1 | 7/2010 | McCaffrey et al. |
| 2010/0167339 A1 | 7/2010 | Clayton et al. |
| 2010/0167381 A1 | 7/2010 | Woerlee et al. |
| 2010/0170149 A1 | 7/2010 | Keeler et al. |
| 2010/0173355 A1 | 7/2010 | Haase et al. |
| 2010/0173375 A1 | 7/2010 | Oyler |
| 2010/0184177 A1 | 7/2010 | Mitchell |
| 2010/0184194 A1 | 7/2010 | Nagnath |
| 2010/0189806 A1 | 7/2010 | Harper et al. |
| 2010/0190227 A1 | 7/2010 | Dauth et al. |
| 2010/0196995 A1 | 8/2010 | Weissman et al. |
| 2010/0203618 A1 | 8/2010 | Rispoli et al. |
| 2010/0210001 A1 | 8/2010 | Seyfried et al. |
| 2010/0210002 A1 | 8/2010 | McCaffrey et al. |
| 2010/0211812 A1 | 8/2010 | Bullen et al. |
| 2010/0216240 A1 | 8/2010 | Moolman et al. |
| 2010/0227368 A1 | 9/2010 | Steiner |
| 2010/0233786 A1 | 9/2010 | O Connor |
| 2010/0233787 A1 | 9/2010 | Halachmi |
| 2010/0233796 A1 | 9/2010 | Kurihara et al. |
| 2010/0267122 A1 | 10/2010 | Chinnasamy et al. |
| 2010/0273210 A1 | 10/2010 | Reddy |
| 2010/0297739 A1 | 11/2010 | Steiner et al. |
| 2010/0297749 A1 | 11/2010 | Aravanis et al. |
| 2011/0014683 A1 | 1/2011 | Vermaas et al. |
| 2011/0020913 A1 | 1/2011 | Rispoli et al. |
| 2011/0023565 A1 | 2/2011 | Yanik et al. |
| 2011/0027827 A1 | 2/2011 | Chi et al. |
| 2011/0113681 A1 | 5/2011 | Mostertz et al. |
| 2011/0124091 A1 | 5/2011 | Lu et al. |
| 2011/0139409 A1 | 6/2011 | Erd |
| 2011/0159581 A1 | 6/2011 | Zhang et al. |
| 2011/0195473 A1 | 8/2011 | Wilhelm |
| 2011/0195493 A1 | 8/2011 | Stroiazzo-Mougin |
| 2011/0236958 A1 | 9/2011 | Wong |
| 2011/0287405 A1 | 11/2011 | Gonzalez et al. |
| 2012/0020228 A1 | 1/2012 | Ding et al. |
| 2012/0156669 A1 | 6/2012 | Gonzalez et al. |
| 2012/0203714 A1 | 8/2012 | Gonzalez et al. |
| 2014/0186931 A1 | 7/2014 | Gonzalez et al. |

FOREIGN PATENT DOCUMENTS

| | | |
|---|---|---|
| CA | 2738410 A1 | 11/2011 |
| CA | 2738418 A1 | 11/2011 |
| CA | 2738459 A1 | 11/2011 |
| CA | 2738461 A1 | 11/2011 |
| CA | 2738516 A1 | 11/2011 |
| CN | 1668185 A | 9/2005 |
| CN | 2749890 Y | 1/2006 |
| CN | 101139113 A | 3/2008 |
| CN | 101254364 A | 9/2008 |
| CN | 101356261 | 1/2009 |
| CN | 101356261 A | 1/2009 |
| CN | 201381254 Y | 1/2010 |
| CN | 101648092 A | 2/2010 |
| CN | 101669569 A | 3/2010 |
| CN | 101696389 | 4/2010 |
| CN | 10326396 | 8/2013 |
| EP | 1072301 | 1/2001 |
| EP | 1072301 A1 | 1/2001 |
| EP | 2422870 | 2/2012 |
| GB | 2458529 A | 9/2009 |
| JP | 3076586 B | 12/1991 |
| JP | 4287678 A | 10/1992 |
| JP | 04084883 B2 | 4/2008 |
| TW | I234235 B | 6/2005 |
| WO | WO1991018108 A1 | 11/1991 |
| WO | WO1998000559 A1 | 1/1998 |
| WO | WO1998028081 A1 | 7/1998 |
| WO | WO1998028082 A1 | 7/1998 |
| WO | WO1998028083 A1 | 7/1998 |
| WO | WO1998028403 A1 | 7/1998 |
| WO | WO1998028404 A1 | 7/1998 |
| WO | WO1999001021 A1 | 1/1999 |
| WO | WO2003038348 A1 | 5/2003 |
| WO | 2003/094598 | 11/2003 |
| WO | WO2005006838 A3 | 8/2005 |
| WO | WO2006020177 A1 | 2/2006 |
| WO | 2007/047805 | 4/2007 |
| WO | WO2007070452 A1 | 6/2007 |
| WO | WO2007134141 A2 | 11/2007 |
| WO | WO2008028143 A2 | 3/2008 |
| WO | WO2008008262 A3 | 4/2008 |
| WO | 2008/079896 | 7/2008 |
| WO | 2008079896 A1 | 7/2008 |
| WO | WO2008089321 A2 | 7/2008 |
| WO | WO2008156795 A1 | 12/2008 |
| WO | WO2008128625 A3 | 1/2009 |
| WO | WO2009015054 A1 | 1/2009 |
| WO | WO2009018498 A2 | 2/2009 |
| WO | WO2008156835 A3 | 3/2009 |
| WO | WO2009094440 A1 | 7/2009 |
| WO | WO2009134358 A1 | 11/2009 |
| WO | 2010/010554 | 1/2010 |
| WO | WO2010002745 A1 | 1/2010 |
| WO | WO2010011320 A1 | 1/2010 |
| WO | WO2010021753 A1 | 2/2010 |
| WO | WO2009142765 A3 | 3/2010 |
| WO | WO2010034023 A1 | 3/2010 |
| WO | WO2010009284 A3 | 4/2010 |
| WO | 2010/094015 | 8/2010 |
| WO | WO 2010/108049 | 9/2010 |
| WO | 2010/123943 | 10/2010 |
| WO | 2011/050578 | 5/2011 |

(56) References Cited

FOREIGN PATENT DOCUMENTS

| WO | 2011/143749 | 11/2011 |
|---|---|---|
| WO | WO 2011/143749 | 11/2011 |

OTHER PUBLICATIONS

Masojidek et al. "A closed solar photobioreactor for cultivation of microalgae under supra-high irradiance basic design and performance" Journal of Applied Phycology [Online] 2003, 15, 239-248.
Berenguel et al. "Model predictive control of pH in tubular photobioreactors" Journal of Process Control, 2004 14, pp. 377-387.
Degen, et al. "A novel airlift photobioreactor with baffles for improved light utilization through the flashing light effect" Journal of Biotechnology, 2001, 92, pp. 89-94.
Putt. "Algae as a Biodiesel Feedstock: A Feasibility Assessment" (Center for Microfibrous Materials Manufacturing, Department of Chemical Engineering, Auburn University, Alabama).
Zebib, "Microalgae Grown in Photobiorecators for Mass Production of Biofuel". Rutger University, Department of Bioenvironmental Engineering, Sep. 2008 http://www.water.rutgers.edu/Educational_Programs/Senior%20Design2008/Algae%20to%20Energy%20Report.pdf.
Wang, et al., "CO2 bio-mitigation using microalgae". Appl. Microbiol. Biotechnol., 2008, vol. 79, pp. 709-718. ISSN: 01757598.
Yang, et al., "Progress in carbon dioxide separation and capture: A review". J.Env. Sci., 2008, vol. 20, pp. 14-27. ISSN: 10010742.
Greenwell, et al., "Placing microalgae on the biofuels priority list: a review of the technological challenges" J. R. Soc. Interface 2010 7, 703-726 first published online Dec. 23, 2009 doi: 10.1098/rsif.2009.0322.
Maeda, et al., "CO2 fixation from the flue gas on coal-fired thermal power plant by microalgae". Energy Convers. Mgmt vol. 36, No. 6-9, pp. 717-720, 1995.
Negoro, et al., "Carbon Dioxide Fixation by Microalgae Photosynthesis Using Actual Flue Gas Discharged from a Boiler". Appl. Biochem. Biotechnol., 1993, vol. 39/40, pp. 643-653. ISSN: 02732289.
Suh, et al., "Photobioreactor Engineering: Design and Performance". Biotechnol. Bioprocess Eng., 2003, vol. 8, No. 6, pp. 313-321. ISSN: 12268372.
O. Pulz "Photobioreactors: production systems for phototrophic microorganisms". Appl. Microbiol. Biotechnol, 2001, vol. 57, pp. 287-293. ISSN: 01757598.
Niels T. Eriksen "The technology of microalgal culturing". Biotechnol Lett., 2008, vol. 30, pp. 1525-1536. ISSN: 01415492.
Carvalho, A.P., et al., "Microalgal Reactors: A Review of Enclosed System Designs and Performances". Biotechnol. Prog., 2006, vol. 22, No. 6, pp. 1490-1506. ISSN: 87567938.
Ishida, M., et al., "CO2 Recovery in a Power Plant with Chemical Looping Combustion". Energy Convers. Mgmt., 1997, vol. 38, Suppl., pp. S187-S192. ISSN: 01968904.
Cote, R. and Wright, R. "Resource Conservation and Industrial Symbiosis: Strategies for enhancing the environmental sustainability of the Keltic Petrochemical Cluster" Prepared by Eco-Efficiency Centre Dalhousie University, on Mar. 29, 2006 (Mar. 29, 2006), Retrieved on Apr. 19, 2012 (Apr. 19, 2012), Retrieved from the internet: <URL: http://eco-efficiency.management.dal.ca/Files/Keltic Petrochemical Cluster.pdf.
Meridian Planning Consultants Inc., "Bruce Energy Center Discussion Paper, Municipality of Kincardine" Prepared by Meridian Planning Consultants Inc. Jun. 2005 (Jun. 2005), Retrieved on Apr. 19, 2012 (Apr. 19, 2012), Retrieved from the internet: <URL: http://www.kincardine.net/public docs/documents/Bruce%20Energy%20C enter%20Discussion%20Paper1.pdf.
Hurst, T., "Canadian Cement Plant Becomes First to Capture CO2 in Algae—A Canadian company called Pond Biofuels is capturing CO2 emissions from a cement plant in algae-algae the company ultimately plans on using to make biofuel." Earth and Industry, Mar. 19, 2010, Retrieved on Apr. 19, 2012, Retrieved from the internet:<URL: http://earthandindustry.com/2010/03/canadian-cement-plant-becomes-first-to-capture-co2-in-algae.
Hamilton, T. "CO2-eating algae turns cement maker green" The Star, Published on Mar. 18, 2010, Retrieved on Apr. 19, 2012, Retrieved from the internet: <URL: http://www.thestar.com/business/article/781426--co2-eating-algae-turns-cement-maker-green.
Janssen M et al., Enclosed outdoor photobireactors: Light regime, photosynthetic efficiency, scale-up, and future prospects. Biotechnology and Bioengineering, vol. 81, Iss. 2, 2003, pp. 193-210.
International Search Report and Written Opinion; Application No. PCT/CA2011/000403; dated Jul. 31, 2012; 12 pages.
Stewart et al., "A Study of Methods of Carbon Dioxide Capture and Sequestration—The Sustainability of a Photosynthetic Bioreactor Approach," Energy Coversion and Management. 46:403-420; 2005.
Patent Office of the Cooperation Council for the Arab States of the Gulf, Office Action for GC Application No. 2012/21131 dated Dec. 19, 2016.
International Search Report and Written Opinion; dated May 23, 2012; World Intellectual Property Organization (WIPO) (International Bureau of); PCT/CA2012/000093; 17 pages.
International Search Report and Written Opinion; dated Sep. 22, 2011; World Intellectual Property Organization (WIPO) (International Bureau of); PCT/CA2011/000574; 21 pages.
International Search Report and Written Opinion; dated May 10, 2012; World Intellectual Property Organization (WIPO) (International Bureau of); PCT/CA2011/000097; 10 pages.
International Search Report and Written Opinion; dated Apr. 19, 2012; World Intellectual Property Organization (WIPO) (International Bureau of); PCT/CA2011/001367; 22 pages.
Eriksen; The technology of microalgal culturing; Biotechnol. Lett.; 2008; 30:1525-1536.
Final Office Action issued in U.S. Appl. No 13/021,489 dated Nov. 29, 2013, (65 pages).
Final Office Action issued in U.S. Appl. No. 13/659,693 dated Feb. 20, 2014, (16 pages).
Hendershot et al., "Use Oxygen to Improve Combustion and Oxidation," American Institute of Chemical Engineers (AIChE), Chemical Engineering Progress, 57-60 (2010).
http://www.britannica.com/EBchecked/topic/108636/chemical-element/81245/Theatmosphere on May 13, 2013.
International Search Report and Written Opinion; Application No. PCT/CA2013/000908; dated Jan. 23, 2014; 12 pages.
International Search Report and Written Opinion; Application No. PCT/CA2013/000904; dated Feb. 7, 2014; 10 pages.
Kunjapur et al., "Photobioreactor Design for Commercial Biofuel Production from Microalgae," Ind. Eng. Chem. Res., 49:3516-3526 (2010).
Myklestad et al., "A photobioreactor with pH control: demonstration by growth of the marine diatom Skeletonema costatum," Journal of Plankton Research, 24(6):557-563 (2002).
Notice of Appeal filed in U.S. Appl. No. 13/327,541, filed Dec. 20, 2013 (1 page).
Office Action issued in U.S. Appl. No. 13/021,489 dated Mar. 18, 2013, (52 pages).
Office Action issued in U.S. Appl. No. 13/022,396 dated Dec. 18, 2012, (19 pages).
Office Action issued in U.S. Appl. No. 13/022,508 dated Feb. 13, 2014 (13 pages).
Office Action issued in U.S. Appl. No. 13/327,541 dated Jun. 27, 2013, (25 pages).
Office Action issued in U.S. Appl. No. 13/327,541 dated Sep. 19, 2012, (22 pages).
Office Action issued in U.S. Appl. No. 13/659,693 dated May 24, 2013, (19 pages).
Office Action issued in U.S. Appl. No. 13/659,714 dated May 24, 2013, (17 pages).
Response to Office Action issued in U.S. Appl. No. 13/021,489 dated Mar. 18, 2013, filed Sep. 18, 2013 (20 pages).
Response to Office Action issued in U.S. Appl. No. 13/327,541 dated Sep. 19, 2012, filed Mar. 19, 2013 (20 pages).
Response to Office Action issued in U.S. Appl. No. 13/659,693 dated May 24, 2013, filed Oct. 24, 2013 (13 pages).

(56) References Cited

OTHER PUBLICATIONS

Response to Restriction Requirement issued in U.S. Appl. No. 13/022,508 dated Sep. 18, 2013, filed Oct. 18, 2013 (1 page).
Restriction Requirement issued in U.S. Appl. No. 13/022,508 dated Sep. 18, 2013, (6 pages).
Sun et al., "An Experiment on Enclosed and Constant Culture of Marine Microalgae," Fisheries Science, 22(3):22-24 (2003).
Office Action issued in CN2014022101011280 dated Feb. 26, 2014 with translation (20 pages).
European Search Report issued in EP 11782806 dated Aug. 1, 2014 (7 pages).
European Search Report issued in EP 11858246 dated Sep. 17, 2014 (6 pages).
Response to Office Action issued in U.S. Appl. No. 13/327,541 dated Sep. 19, 2014, filed Mar. 19, 2015 (16 pages).
Response to Office Action issued in U.S. Appl. No. 13/022,508 dated Nov. 6, 2014, filed Apr. 6, 2015 (13 pages).
Chinese Office Action (with English translation) issued in CN 201180035594, dated Jan. 16, 2015 (22 pages).
Chinese Office Action (with English Tranlation) issued in CN 2014091901006550, dated Sep. 24, 2014 (25 pages).
Chinese Office Action (with English Translation) issued in CN 201280031706.3, dated Jan. 9, 2015 (12 pages).
Shi et al., "Effects of the pH/$pCO_2$ control method on medium chemistry and phytoplankton growth," Biogeosciences, 6:1199-1207 (2009).
Sun et al., "An Experiment on Enclosed and Constant Culture of Marine Microalgae," Fisheries Science, 22(3):22-24 (2003) (Translation).
European Search Report issued in EP 12776555 dated Dec. 22, 2014 (6 pages).
Herzog et al., "Advanced Post-Combustion $CO_2$ Capture" Clean Air Task Force, Apr. 2009, 39 pages.
Office Action issued in U.S. Appl. No. 14/089,278 dated Jan. 12, 2015, (16 pages).
Final Office Action issued in U.S. Appl. No. 13/022,508 dated Nov. 6, 2014, (10 pages).
Office Action issued in U.S. Appl. No. 13/021,489 dated Dec. 4, 2014, (75 pages).
Office Action issued in U.S. Appl. No. 13/327,541 dated Sep. 19, 2014, (16 pages).
State Intellectual Property Office of P.R.C, Office Action for CN Application No. 2012800317063 dated Jan. 9, 2015.
State Intellectual Property Office of P.R.C, Office Action for CN Application No. 2012800317063 dated Sep. 14, 2015.
European Patent Office, Extended European Search Report for EP Application No. 12776555.0 dated Dec. 22, 2014.
Herzog et al., Advanced Post-Combustion CO2 Capture, Clean Air Task Force under a grant from the Doris Duke Foundation, Apr. 2009, pp. 1-38.
European Patent Office, Office Action for EP Application No. 12776555.0 dated Mar. 22, 2016.
WIPO, International Search Report and Written Opinion for PCT Application No. PCT/CA2012/000403 dated Jul. 31, 2012.
Stewart, C., et al., "A study of methods of carbon dioxide capture and sequestration—the sustainability of a photosynthetic bioreactor approach", Energy Conversion and Management, 2005, vol. 46, pp. 403-420.
Taiwan Intellectual Property Office, Office Action for TW Application No. 101114893 dated Feb. 22, 2016.
USPTO, Office Action for U.S. Appl. No. 13/095,490 dated Oct. 8, 2014.
USPTO, Office Action for U.S. Appl. No. 13/095,490 dated Jul. 8, 2015.
Taiwanese Office Action (with English Translation) issued in TW 10117390, dated Jun. 2, 2015 (19 pages).
Patent Office of the Cooperation Council for the Arab States of the Gulf, Examination Report or GC Application No. 2012-21131 dated May 9, 2017.

\* cited by examiner

SUPPLYING TREATED EXHAUST GASES FOR EFFECTING GROWTH OF PHOTOTROPHIC BIOMASS

CROSS-REFERENCE TO RELATED APPLICATION

This application is a continuation of U.S. application Ser. No. 13/095,490, filed Apr. 27, 2011.

FIELD

The present disclosure relates to a process for growing biomass.

BACKGROUND

The cultivation of phototrophic organisms has been widely practised for purposes of producing a fuel source. Exhaust gases from industrial processes have also been used to promote the growth of phototrophic organisms by supplying carbon dioxide for consumption by phototrophic organisms during photosynthesis. By providing exhaust gases for such purpose, environmental impact is reduced and, in parallel a potentially useful fuel source is produced. Challenges remain, however, to render this approach more economically attractive for incorporation within existing facilities.

SUMMARY

In one aspect, there is provided a process for growing a phototrophic biomass in a reaction zone. The process includes treating an operative carbon dioxide supply-comprising gaseous material feed so as to effect production of a carbon dioxide-rich product material. The carbon dioxide concentration of the carbon dioxide-rich product material is greater than the carbon dioxide concentration of the operative carbon dioxide supply-comprising gaseous material feed. Production of at least a fraction of the operative carbon dioxide supply-comprising gaseous material feed is effected by a gaseous exhaust material producing process. At least a fraction of the carbon dioxide-rich product material is supplied to the reaction zone so as to effect growth of the phototrophic biomass by photosynthesis in the reaction zone.

BRIEF DESCRIPTION OF THE DRAWINGS

The process of the preferred embodiments of the invention will now be described with the following accompanying drawing.

DETAILED DESCRIPTION

Reference throughout the specification to "some embodiments" means that a particular feature, structure, or characteristic described in connection with some embodiments are not necessarily referring to the same embodiments. Furthermore, the particular features, structure, or characteristics may be combined in any suitable manner with one another.

Figure 1:
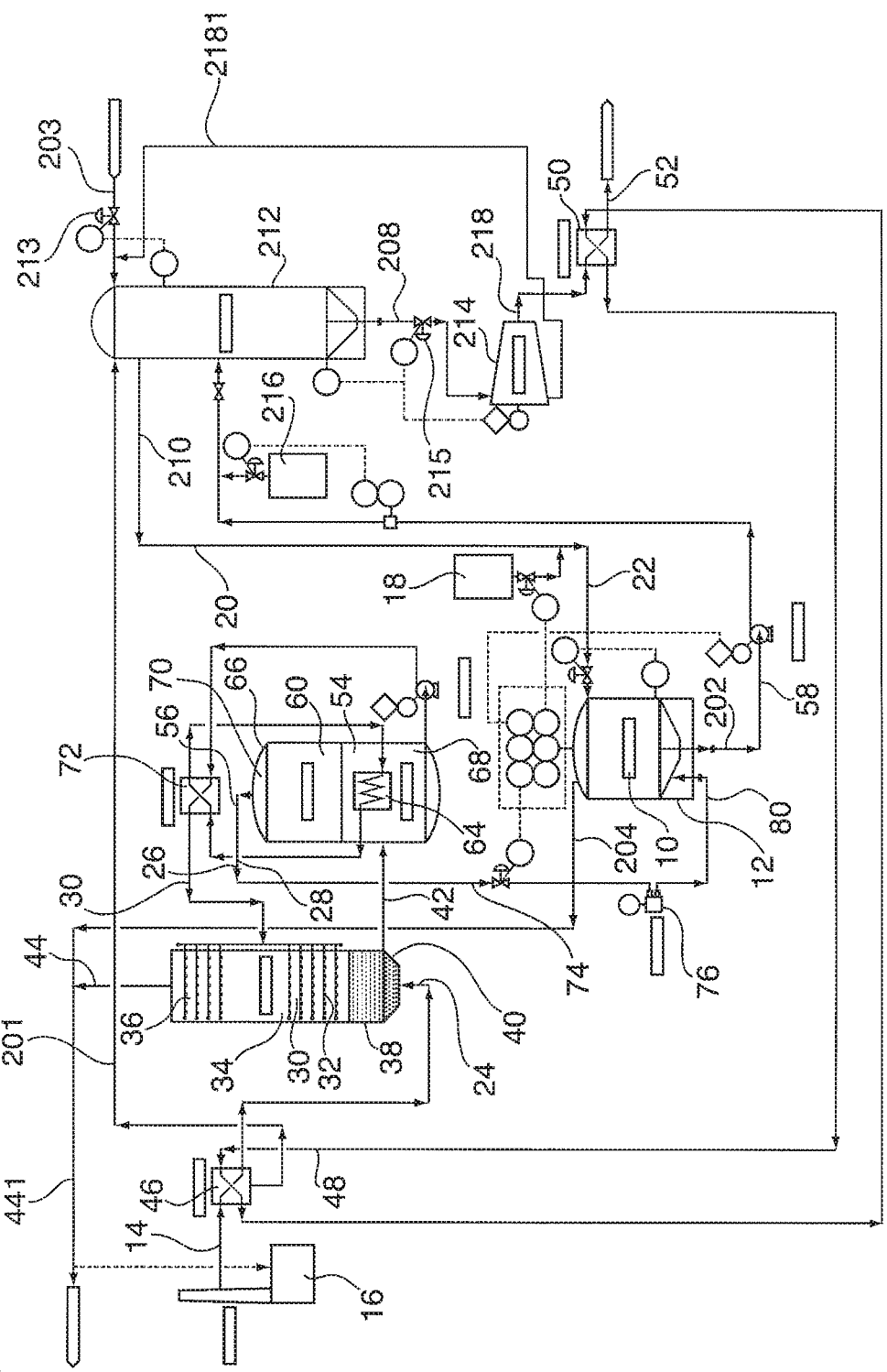
FIG. 1 is a process flow diagram of an embodiment of the process.
Figure 2:
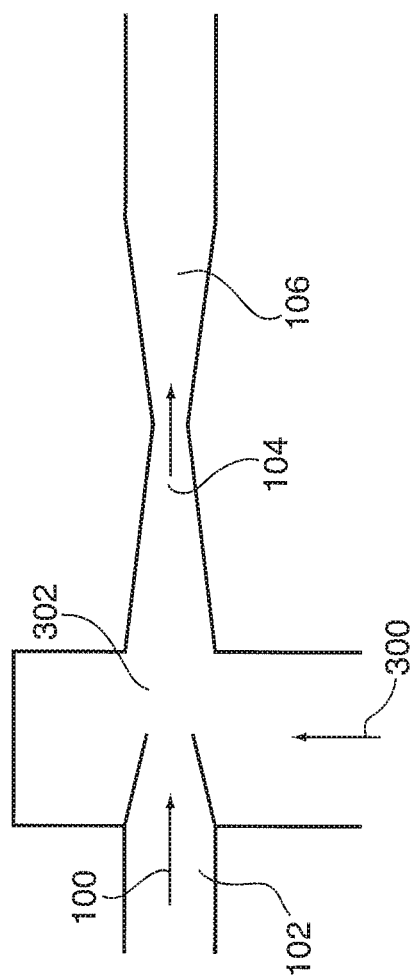
FIG. 2 is a schematic illustration of a portion of a fluid passage of an embodiment of the process.

Referring to FIG. 1, there is provided a process of growing a phototrophic biomass in a reaction zone 10. The reaction zone 10 includes a reaction mixture that is operative for effecting photosynthesis upon exposure to photosynthetically active light radiation. The reaction mixture includes phototrophic biomass material, carbon dioxide, and water. In some embodiments, the reaction zone includes phototrophic biomass and carbon dioxide disposed in an aqueous medium. Within the reaction zone 10, the phototrophic biomass is disposed in mass transfer communication with both of carbon dioxide and water.

"Phototrophic organism" is an organism capable of phototrophic growth in the aqueous medium upon receiving light energy, such as plant cells and micro-organisms. The phototrophic organism is unicellular or multicellular. In some embodiments, for example, the phototrophic organism is an organism which has been modified artificially or by gene manipulation. In some embodiments, for example, the phototrophic organism is an algae. In some embodiments, for example, the algae is microalgae.

"Phototrophic biomass" is at least one phototrophic organism. In some embodiments, for example, the phototrophic biomass includes more than one species of phototrophic organisms.

"Reaction zone 10" defines a space within which the growing of the phototrophic biomass is effected. In some embodiments, for example, the reaction zone 10 is provided in a photobioreactor 12. In some embodiments, for example, pressure within the reaction zone is atmospheric pressure.

"Photobioreactor 12" is any structure, arrangement, land formation or area that provides a suitable environment for the growth of phototrophic biomass. Examples of specific structures which can be used is a photobioreactor 12 by providing space for growth of phototrophic biomass using light energy include, without limitation, tanks, ponds, troughs, ditches, pools, pipes, tubes, canals, and channels. Such photobioreactors may be either open, closed, partially closed, covered, or partially covered. In some embodiments, for example, the photobioreactor 12 is a pond, and the pond is open, in which case the pond is susceptible to uncontrolled receiving of materials and light energy from the immediate environments. In other embodiments, for example, the photobioreactor 12 is a covered pond or a partially covered pond, in which case the receiving of materials from the immediate environment is at least partially interfered with. The photobioreactor 12 includes the reaction zone 10 which includes the reaction mixture. In some embodiments, the photobioreactor 12 is configured to receive a supply of phototrophic reagents (and, in some of these embodiments, optionally, supplemental nutrients), and is also configured to effect discharge of phototrophic biomass which is grown within the reaction zone 10. In this respect, in some embodiments, the photobioreactor 12 includes one or more inlets for receiving the supply of phototrophic reagents and supplemental nutrients, and also includes one or more outlets for effecting the recovery or harvesting of biomass which is grown within the reaction zone 10. In some embodiments, for example, one or more of the inlets are configured to be temporarily sealed for periodic or intermittent time intervals. In some embodiments, for example, one or more of the outlets are configured to be temporarily sealed or substantially sealed for periodic or intermittent time intervals. The photobioreactor 12 is configured to contain the reaction mixture which is operative for effecting photosynthesis upon exposure to photosynthetically active light radiation. The photobioreactor 12 is also configured so as to establish photosynthetically active light radiation (for example, a light of a wavelength between about 400-700 nm, which can be emitted by the sun or another light source) within the photobioreactor 12 for exposing the phototrophic biomass. The exposing of the reaction mixture to the photosynthetically active light radiation effects photosynthesis and growth of the phototrophic biomass. In some embodiments, for example, the established light radiation is provided by an artificial light source 14 disposed within the photobioreactor 12. For example, suitable artificial lights sources include submersible fiber optics or light guides, light-emitting diodes ("LEDs"), LED strips and fluorescent lights. Any LED strips known in the art can be adapted for use in the photobioreactor 12. In the case of the submersible LEDs, in some embodiments, for example, energy sources include alternative energy sources, such as wind, photovoltaic cells, fuel cells, etc. to supply electricity to the LEDs. Fluorescent lights, external or internal to the photobioreactor 12, can be used as a back-up system. In some embodiments, for example, the established light is derived from a natural light source 16 which has been transmitted from externally of the photobioreactor 12 and through a transmission component. In some embodiments, for example, the transmission component is a portion of a containment structure of the photobioreactor 12 which is at least partially transparent to the photosynthetically active light radiation, and which is configured to provide for transmission of such light to the reaction zone 10 for receiving by the phototrophic biomass. In some embodiments, for example, natural light is received by a solar collector, filtered with selective wavelength filters, and then transmitted to the reaction zone 10 with fiber optic material or with a light guide. In some embodiments, for example, both natural and artificial lights sources are provided for effecting establishment of the photosyntetically active light radiation within the photobioreactor 12.

"Aqueous medium" is an environment that includes water. In some embodiments, for example, the aqueous medium also includes sufficient nutrients to facilitate viability and growth of the phototrophic biomass. In some embodiments, for example, supplemental nutrients may be included such as one of, or both of, $NO_x$ and $SO_x$. Suitable aqueous media are discussed in detail in: Rogers, L. J. and Gallon J. R. "Biochemistry of the Algae and Cyanobacteria," Clarendon Press Oxford, 1988; Burlew, John S. "Algal Culture: From Laboratory to Pilot Plant." Carnegie Institution of Washington Publication 600. Washington, D.C., 1961 (hereinafter "Burlew 1961"); and Round, F. E. The Biology of the Algae. St Martin's Press, New York, 1965; each of which is incorporated herein by reference). A suitable supplemental nutrient composition, known as "Bold's Basal Medium", is described in Bold, H. C. 1949, *The morphology of Chlamydomonas chlamydogama sp. nov. Bull. Torrey Bot. Club.* 76: 101-8 (see also Bischoff, H. W. and Bold, H. C. 1963. *Phycological Studies IV. Some soil algae from Enchanted Rock and related algal species*, Univ. Texas Publ. 6318: 1-95, and Stein, J. (ED.) *Handbook of Phycological Methods, Culture methods and growth measurements*, Cambridge University Press, pp. 7-24).

The process includes supplying the reaction zone 10 with carbon dioxide derived from a gaseous exhaust material 14 being discharged by a gaseous exhaust material producing process 16. The gaseous exhaust material 14 includes carbon dioxide, and the carbon dioxide of the gaseous exhaust material defines produced carbon dioxide.

In some embodiments, for example, the gaseous exhaust material 14 includes a carbon dioxide concentration of at least two (2) volume % based on the total volume of the gaseous exhaust material 14. In some embodiments, for example, the gaseous exhaust material 14 includes a carbon dioxide concentration of at least four (4) volume % based on the total volume of the gaseous exhaust material 14. In some embodiments, for example, the gaseous exhaust material reaction 14 also includes one or more of $N_2$, $CO_2$, $H_2O$, $O_2$, $NO_x$, $SO_x$, CO, volatile organic compounds (such as those from unconsumed fuels) heavy metals, particulate matter, and ash. In some embodiments, for example, the gaseous exhaust material 14 includes 30 to 60 volume % $N_2$ 5 to 25 volume % $O_2$, 2 to 50 volume % $CO_2$, and 0 to 30 volume % $H_2O$, based on the total volume of the gaseous exhaust material 14. Other compounds may also be present, but usually in trace amounts (cumulatively, usually less than five (5) volume % based on the total volume of the gaseous exhaust material 14).

In some embodiments, for example, the gaseous exhaust material 14 includes one or more other materials, other than carbon dioxide, that are beneficial to the growth of the phototrophic biomass within the reaction zone 10. Materials within the gaseous exhaust material which are beneficial to the growth of the phototrophic biomass within the reaction zone 10 include $SO_x$, $NO_x$, and $NH_3$.

In some embodiments, for example, a supplemental nutrient supply 18 is supplied to the reaction zone 10. In some embodiments, for example, the supplemental nutrient supply 18 is effected by a pump, such as a dosing pump. In other embodiments, for example, the supplemental nutrient supply 18 is supplied manually to the reaction zone 10. Nutrients within the reaction zone 10 are processed or consumed by the phototrophic biomass, and it is desirable, in some circumstances, to replenish the processed or consumed nutrients. A suitable nutrient composition is "Bold's Basal Medium", and this is described in Bold, H. C. 1949, *The morphology of Chlamydomonas chlamydogama sp. nov. Bull. Torrey Bot. Club.* 76: 101-8 (see also Bischoff, H. W. and Bold, H. C. 1963. *Phycological Studies IV. Some soil algae Enchanted Rock and related algal species*, Univ. Texas Publ, 6318: 1-95; and Stein, J. (ED.) *Handbook of Phycological Methods, Culture methods and growth measurements*, Cambridge University Press, pp. 7-24). The supplemental nutrient supply 18 is supplied for supplementing the nutrients provided within the reaction zone, such as "Bold's Basal Medium", or one ore more dissolved components thereof. In this respect, in some embodiments, for example, the supplemental nutrient supply 18 includes "Bold's Basal Medium". In some embodiments for example, the supplemental nutrient supply 18 includes one or more dissolved components of "Bold's Basal Medium", such as $NaNO_3$, $CaCl_2$, $MgSO_4$, $KH_2PO_4$, NaCl, or other ones of its constituent dissolved components.

In some of these embodiments, the rate of supply of the supplemental nutrient supply 18 to the reaction zone 10 is controlled to align with a desired rate of growth of the phototrophic biomass in the reaction zone 10. In some embodiments, for example, regulation of nutrient addition is monitored by measuring any combination of pH, $NO_3$ concentration, and conductivity in the reaction zone 10.

In some embodiments, for example, a supply of the supplemental aqueous material supply 20 is effected to the reaction zone 10 so as to replenish water within the reaction zone 10 of the photobioreactor 12. In some embodiments, for example, and as further described below, the supplemental aqueous material supply 20 effects the discharge of product from the photobioreactor 12 by displacement. For example, the supplemental aqueous material supply 20 effects the discharge of product from the photobioreactor 12 as an overflow.

In some embodiments, for example, the supplemental aqueous material is water or substantially water. In some embodiments, for example, the supplemental aqueous material supply 20 includes at least one of: (a) aqueous material that has been condensed from the supplied exhausted carbon dioxide while the supplied exhausted carbon dioxide is being cooled before being supplied to the contacting zone 34, and (b) aqueous material that has been separated from a discharged phototrophic biomass-comprising product 202 (see below). In some embodiments, for example, the supplemental aqueous material supply 20 is derived from an independent source (ie. a source other than the process), such as a municipal water supply 203.

In some embodiments, for example, the supplemental aqueous material supply 20 is supplied from a container that has collected aqueous material recovered from discharges from the process, such as: (a) aqueous material that has been condensed from the supplied exhausted carbon dioxide while the supplied exhausted carbon dioxide is being cooled before being supplied to the contacting zone, and (b) aqueous material that has been separated from a discharged phototrophic biomass-comprising product 202. In some embodiments, for example, the container is in the form of a settling column 212 (see below).

In some embodiments, for example, the supplemental nutrient supply 18 is mixed with the supplemental aqueous material 20 to provide a nutrient-enriched supplemental aqueous material supply 22, and the nutrient-enriched supplemental aqueous material supply 22 is supplied to the reaction zone 10. In some embodiments, for example, the supplemental nutrient supply 18 is mixed with the supplemental aqueous material 20 within the container which has collected the discharged aqueous material. In some embodiments, for example, the supply of the nutrient-enriched supplemental aqueous material supply 18 is effected by a pump.

An operative carbon dioxide supply-comprising gaseous material feed is provided. The operative carbon dioxide supply-comprising gaseous material feed includes carbon dioxide and one or more other materials. The operative carbon dioxide supply-comprising gaseous material feed includes at least a fraction of the gaseous exhaust material 14, and the at least a fraction of the gaseous exhaust material 14 of the operative carbon dioxide supply-comprising gaseous material feed defines supplied gaseous exhaust material. The carbon dioxide that is supplied to the operative carbon dioxide supply-comprising gaseous material feed from the gaseous exhaust material producing process 16 defines supplied exhausted carbon dioxide. The supplied exhausted carbon dioxide is defined by at least a fraction of the produced carbon dioxide. The carbon dioxide of the operative carbon dioxide supply-comprising gaseous material feed includes supplied exhausted carbon dioxide. In some embodiments, for example, the carbon dioxide of the operative carbon dioxide supply-comprising gaseous material feed is defined by the supplied exhausted carbon dioxide. In some embodiments, for example, the operative carbon dioxide supply-comprising gaseous material feed is defined by supplied gaseous exhaust material.

In some embodiments, for example, the operative carbon dioxide supply-comprising gaseous material feed includes one or more other materials supplied from the gaseous exhaust material 14, other than carbon dioxide, that are beneficial to the growth of the phototrophic biomass within the reaction zone 10. Examples of such materials include $SO_x$, $NO_x$, and $NH_3$.

The gaseous exhaust material producing process 16 includes any process which effects production and discharge of the gaseous exhaust material 14. In some embodiments, for example, at least a fraction of the gaseous exhaust material 14 being discharged by the gaseous exhaust material producing process 16 is supplied to the reaction zone 10. The at least a fraction of the gaseous exhaust material 14, being discharged by the gaseous exhaust material producing process 16, and supplied to the reaction zone 10, includes carbon dioxide derived from the gaseous exhaust material producing process 16. In some embodiments, for example, the gaseous exhaust material producing process 16 is a combustion process. In some embodiments, for example, the combustion process is effected in a combustion facility. In some of these embodiments, for example, the combustion process effects combustion of a fossil fuel, such as coal, oil, or natural gas. For example, the combustion facility is any one of a fossil fuel-fired power plant, an industrial incineration facility, an industrial furnace, an industrial heater, or an internal combustion engine. In some embodiments, for example, the combustion facility is a cement kiln.

The operative carbon dioxide supply-comprising gaseous material feed is treated so as to effect production of a carbon dioxide-rich product material 26. In some embodiments, the carbon dioxide-rich product material 26 is gaseous. The carbon dioxide of the carbon dioxide-rich product material 26 defines concentrated reaction zone supply carbon dioxide. The carbon dioxide concentration of the carbon dioxide-rich product material 26 is greater than the carbon dioxide concentration of the operative carbon dioxide supply-comprising gaseous material feed. The carbon dioxide-rich product material 26 includes at least a fraction of the supplied exhausted carbon dioxide, such that the concentrated reaction zone supply carbon dioxide includes at least a fraction of the supplied exhausted carbon dioxide. In some embodiments, the concentrated reaction zone supply carbon dioxide is defined by at least a fraction of the supplied exhausted carbon dioxide. As such, the carbon dioxide-rich product material 26 includes at least a fraction of the produced carbon dioxide, such that the concentrated reaction zone supply carbon dioxide includes at least a fraction of produced carbon dioxide. In some embodiments, the concentrated reaction zone supply carbon dioxide is defined by at least a fraction of the produced carbon dioxide.

In some embodiments, for example, the carbon dioxide-rich product material 26 includes one or more other materials supplied from the gaseous exhaust material 14, other than carbon dioxide, that are beneficial to the growth of the phototrophic biomass within the reaction zone 10. Examples of such materials include $SO_x$, $NO_x$, and $NH_3$.

In some embodiments, the treating of the operative carbon dioxide supply-comprising gaseous material feed includes effecting separation, from a separation process feed material 24, of a carbon dioxide-rich separation fraction 28. The separation process feed material 24 is defined by at least a fraction of the operative carbon dioxide supply-comprising gaseous material feed 24. The carbon dioxide-rich product material 26 includes at least a fraction of the carbon dioxide-rich separation fraction 28. In some embodiments, for example, the carbon dioxide-rich separation fraction 28 is gaseous. The carbon dioxide of the carbon dioxide-rich separation fraction 28 includes at least a fraction of the supplied exhausted carbon dioxide, and, in some embodiments, for example, is defined by at least a fraction of the supplied exhausted carbon dioxide. As such, the carbon dioxide of the carbon dioxide-rich separation fraction 28 includes at least a fraction of the produced carbon dioxide, and, in some embodiments, for example, the carbon dioxide of the carbon dioxide-rich separation fraction 28 is defined by at least a fraction of the produced carbon dioxide. In some embodiments, for example, the carbon dioxide-rich separation fraction 28 includes one or more other materials supplied from the gaseous exhaust material 14, other than carbon dioxide, that are beneficial to the growth of the phototrophic biomass within the reaction zone 10. Examples of such materials include $SO_x$, $NO_x$, and $NH_3$.

In some embodiments, for example, the separation process feed material 24 includes one or more other materials, other than carbon dioxide. In some embodiments, for example, the one or more other materials of the separation process feed material 24 are supplied from the gaseous exhaust material 14 and are beneficial to the growth of the phototrophic biomass within the reaction zone 10. Examples of such materials include $SO_x$, $NO_x$, and $NH_3$.

The ratio of [moles of carbon dioxide within the carbon dioxide-rich separation fraction 28] to [moles of the one or more other materials of the separation process feed material 24 within the carbon dioxide-rich separation fraction 28] is greater than the ratio of [moles of carbon dioxide within the separation process feed material 24] to [moles of the one or more other materials of the separation process feed material 24 within the separation process feed material 24]. In some embodiments, for example, the concentration of carbon dioxide within the carbon dioxide-rich fraction 28 is greater than the concentration of carbon dioxide within the separation process feed material 24.

The carbon dioxide-rich product material 26 includes at least a fraction of the carbon dioxide of the carbon dioxide-rich separation fraction 28, such that the concentrated reaction zone supply carbon dioxide includes at least a fraction of the carbon dioxide of the carbon dioxide-rich separation fraction 28. In some embodiments, for example, the concentrated reaction zone supply carbon dioxide is defined by at least a fraction of the carbon dioxide of the carbon dioxide-rich separation fraction 28.

In some embodiments, for example, the effecting separation, from the separation process feed material, of a carbon dioxide-rich separation fraction 28, includes contacting the separation process feed material 24 with an operative solvation (or dissolution) agent 30, so as to effect production of an intermediate operative carbon dioxide supply-comprising mixture 32 including dissolved carbon dioxide. The contacting effects solvation (or dissolution) of at least a fraction of the supplied exhausted carbon dioxide within the operative solvation agent, and thereby effects production of the dissolved carbon dioxide. In some embodiments, for example, the contacting also effects solvation (or dissolution) of at least a fraction of the one or more other materials within the separation process feed material 24. In some embodiments, for example, the one or more other materials that are solvated (or dissolved) are beneficial to the growth of the phototrophic biomass within the reaction zone 10. Examples of such materials include $SO_x$, $NO_x$, and $NH_3$.

The intermediate operative carbon dioxide supply-comprising mixture 32 includes a carbon dioxide-comprising solution intermediate, wherein the carbon dioxide-comprising solution intermediate includes the dissolved carbon dioxide. The dissolved carbon dioxide includes at least a fraction of the supplied exhausted carbon dioxide, and, in some embodiments, is defined by at least a fraction of the supplied exhausted carbon dioxide. In this respect, the dissolved carbon dioxide includes at least a fraction of the produced carbon dioxide, and in some embodiments, is defined by at least a fraction of the produced carbon dioxide. In some embodiments, for example, the carbon dioxide-comprising solution intermediate also includes the one or more other materials supplied by the separation process feed material 24 that are solvated (or dissolved) and that are beneficial to the growth of the phototrophic biomass within the reaction zone 10. Examples of such materials include $SO_x$, $NO_x$, and $NH_3$.

It is understood that the contacting may also effect solvation (or dissolution) of at least a fraction of the one or more other materials of the separation process feed material 24, but only to an extent that the above-described relationship of the ratio of [moles of carbon dioxide within the carbon dioxide-rich separation fraction 28] to [moles of the one or more other materials of the separation process feed material 24 within the carbon dioxide-rich separation fraction 28] and the ratio of [moles of carbon dioxide within the separation process feed material 24] to [moles of the one or more other materials of the separation process feed material within the separation process feed material 24] is maintained.

The contacting also effects production of a carbon dioxide-depleted gaseous intermediate, such that the intermediate operative carbon dioxide supply-comprising mixture 32 includes the carbon dioxide-depleted gaseous intermediate. The carbon dioxide-depleted gaseous intermediate includes a fraction of the separation process feed material 24. The ratio of [moles of carbon dioxide within the separation process feed material 24] to [moles of the other one or more materials of the separation process feed material 24 within the separation process feed material feed 24] is greater than the ratio of [moles of carbon dioxide within the carbon dioxide-depleted gaseous intermediate] to [moles of the other one or more materials of the separation process feed material 24 within the carbon dioxide-depleted gaseous intermediate].

In some embodiments, for example, the contacting of the separation process feed material 24 with an operative solvation (or dissolution) agent 26 effects solvation (or dissolution) of a fraction of the separation process feed material 24 such that a material depleted operative carbon dioxide supply-comprising gaseous material feed is provided, and the material depleted operative carbon dioxide supply-comprising gaseous material feed includes, and, in some embodiments, is defined by, the carbon dioxide-depleted gaseous intermediate.

In some embodiments, for example, the one or more other materials of the separation process feed material 24 includes at least one relatively less soluble material. Relative to carbon dioxide, each one of the at least one relatively less soluble material is less soluble within the operative solvation (or dissolution) agent, when the operative solvation (or dissolution) agent is disposed within the contacting zone. Examples of the relatively less soluble material include $N_2$, $O_2$, and CO.

In some embodiments, for example, the contacting is effected in a contacting zone 34.

In some embodiments, for example, the operative solvation (or dissolution) agent 30 is aqueous material. In some embodiments, for example, the operative solvation (or dissolution) agent 30 is water or substantially water, and the contacting is effected in a contacting zone 34 including a pressure of between 10 psia and 25 psia and a temperature of between two (2) degrees Celsius and four (4) degrees Celsius. In some embodiments, for example, the pressure is atmospheric and the temperature is three (3) degrees Celsius.

In some embodiments, for example, the operative solvation (or dissolution) agent 30 is provided within the contacting zone 34 in the form of a mist by supplying the operative solvation (or dissolution) agent 34 to the contacting zone 34 through a spray nozzle 36. In some embodiments, for example, the spray nozzle 36 includes a plurality of substantially uniformly spaced-apart nozzles to maximize volumetric exchange of gas into the water droplets. Providing the operative solvation (or dissolution) agent 30 in the form of a mist increases the contact surface area between the operative solvation (or dissolution) agent 30 and the separation process feed material 24 being contacted. In some embodiments, for example, the operative solvation (or dissolution) agent discharging from the spray nozzle 36 includes a droplet size of between 10 and 2000 microns. In some embodiments, the operative solvation (or dissolution) agent 30 is discharged through the spray nozzle 36 at a temperature of between two (2) degrees Celsius and four (4) degrees Celsius. In some embodiments, for example, the temperature of the discharged operative solvation (or dissolution) agent is three (3) degrees Celsius.

In some embodiments, for example, the contacting zone 34 is provided within a contacting tank 38. In some embodiments, for example, the contacting tank 38 contains a contacting zone liquid material 40 disposed within the contacting zone. In some embodiments, for example, the contacting zone liquid material 40 includes a vertical extent of between one (1) foot and five (5) feet. In some embodiments, for example, the contacting zone liquid material 40 is disposed at the bottom of the contacting tank 38. The contacting zone liquid material 40 includes the operative solvation (or dissolution) agent 30. In some embodiments, for example, the contacting zone liquid material 40 includes at least a fraction of the operative solvation (or dissolution) agent 30 that has been introduced to the contacting zone 34 through the spray nozzle 36. In some of these embodiments, for example, the contacting zone liquid material 40 includes at least a fraction of the operative solvation (or dissolution) agent 30 that has been introduced to the contacting zone 34 through the spray nozzle 36 and has collected at the bottom of the contacting zone tank 38. In some embodiments, for example, the contacting zone liquid material 40 includes at least a fraction of the carbon dioxide-comprising solution intermediate. In some of these embodiments, for example, the contacting zone liquid material 40 includes carbon dioxide-comprising solution intermediate that has collected at the bottom of the contacting zone tank 38. The separation feed material 24 is flowed through the contacting zone liquid material 40 upon its introduction to the contacting zone 34. In some embodiments, for example, the separation feed material 24 is introduced to the contacting zone liquid material 40 through a sparger.

Separation of a carbon dioxide-comprising liquid solution product 42 is effected from the intermediate operative carbon dioxide supply-comprising mixture 32. The carbon dioxide-comprising liquid solution product 42 includes at least a fraction of the carbon dioxide-comprising solution intermediate, and, in some embodiments, is defined by at least a fraction of the carbon dioxide-comprising solution intermediate, such that the carbon dioxide-comprising liquid solution product 42 includes at least a fraction of the supplied exhausted carbon dioxide, and, in this respect, includes at least a fraction of the produced carbon dioxide. In this respect, the carbon dioxide of the carbon dioxide-comprising liquid solution product 42 includes at least a fraction of the supplied exhausted carbon dioxide, and, in some embodiments, is defined by at least a fraction of the supplied exhausted carbon dioxide. Also in this respect, the carbon dioxide of the carbon dioxide-comprising liquid solution product 42 includes at least a fraction of the produced carbon dioxide, and, in some embodiments, is defined by at least a fraction of the produced carbon dioxide.

In some embodiments, for example, the carbon dioxide-comprising liquid solution product 42 includes the one or more other materials supplied by the separation process feed material 24 that are solvated (or dissolved) within the contacting zone 34 and that are beneficial to the growth of the phototrophic biomass within the reaction zone 10. Examples of such materials include $SO_x$, $NO_x$, and $NH_3$.

In some embodiments, for example, the carbon dioxide-comprising liquid solution product 42 includes dissolved carbon dioxide and at least one of $SO_x$ and $NO_x$.

In some embodiments, for example, the separation of the carbon dioxide-comprising liquid solution product 42 from the intermediate operative carbon dioxide supply-comprising mixture 32 includes separation by gravity separation. In some embodiments, for example, the separation is effected in the contacting zone 34.

In some embodiments, for example, the separation of the carbon dioxide-comprising liquid solution product 42 from the intermediate operative carbon dioxide supply-comprising mixture 32 effects separation of a gaseous contacting operation by-product 44 from the carbon dioxide-comprising liquid solution product 42. The gaseous contacting operation by-product 44 includes at least a fraction of the carbon dioxide-depleted gaseous intermediate, and, in some embodiments, for example, is defined by at least a fraction of the carbon dioxide-depleted gaseous intermediate.

In some embodiments, for example, in parallel with the separation of the carbon dioxide-comprising liquid solution product 42 from the intermediate operative carbon dioxide supply-comprising mixture 32, depletion of the carbon dioxide, and, in some embodiments, of one or more other materials, from within the intermediate operative carbon dioxide supply-comprising mixture 32 is effected, such that separation of a material depleted intermediate operative carbon dioxide supply-comprising mixture from the carbon dioxide-comprising liquid solution product 42 is effected, wherein the material depleted intermediate operative carbon dioxide supply-comprising mixture includes the gaseous contacting operation by-product 44. In some embodiments, for example, the material depleted intermediate operative carbon dioxide supply-comprising mixture is defined by the gaseous contacting operation by-product 44.

In some embodiments, for example, the gaseous contacting operation by-product 44 includes $N_2$, $O_2$, and CO. In some embodiments, for example, the gaseous contacting operation by-product 44 is discharged from the contacting tank as an exhaust 441.

In some embodiments, for example, the supplied gaseous exhaust material, either by itself or as part of the separation process feed material 24, is cooled prior to the separation of a carbon dioxide-rich separation fraction 28 from the separation process feed material 24. In some embodiments, for example, the supplied gaseous exhaust material is cooled prior to supply to the contacting zone 34 so as to facilitate the solvation (or the dissolution) of the carbon dioxide. In some embodiments, for example, the cooling of the supplied gaseous exhaust material facilitates the provision of a material supply to the reaction zone 10 with a temperature that is suitable for the growth of the phototrophic biomass. In some embodiments, for example, the supplied gaseous exhaust material is disposed at a temperature of between 110 degrees Celsius and 150 degrees Celsius. In some embodiments, for example, the temperature of the supplied gaseous exhaust material is about 132 degrees Celsius. In some embodiments, the temperature at which the supplied gaseous exhaust material is disposed is much higher than this, and, in some embodiments, such as the gaseous exhaust material 14 from a steel mill, the temperature can be as high as 500 degrees Celsius. In some embodiments, for example, the cooling is effected so as to facilitate the solvation (or the dissolution) of the carbon dioxide. In some embodiments, for example, the supplied gaseous exhaust material is cooled to 50 degrees Celsius or less (in some embodiments, for example, this depends on the dew point of the water vapour within the supplied gaseous exhaust material). In some of these embodiments, in effecting the cooling of the supplied gaseous exhaust material, at least a fraction of any water vapour of the supplied gaseous exhaust material is condensed in a heat exchanger 46 (such as a condenser) and separated from the supplied gaseous exhaust material as an aqueous material 201. In some embodiments, the resulting aqueous material 201 is re-used in the process. In some embodiments, for example, the resulting aqueous material 201 is re-used as supplemental aqueous material supply 20. In some embodiments, for example, the aqueous material is supplied to the settling column 212 (described below). In some embodiments, the condensing effects heat transfer from the supplied gaseous exhaust material to a heat transfer medium 68, thereby raising the temperature of the heat transfer medium 48 to produce a heated heat transfer medium 48, and the heated heat transfer medium 48 is then supplied (for example, flowed) to a dryer 50 (discussed below), and heat transfer is effected from the heated heat transfer medium 48 to a phototrophic biomass-rich intermediate product that has been derived from a discharge from the photobioreactor to effect drying of the phototrophic biomass-rich intermediate product and thereby effect production of the final reaction zone product 52. In some embodiments, for example, after being discharged from the dryer 50, the heat transfer medium 48 is recirculated to the heat exchanger 46. Examples of a suitable heat transfer medium 48 include thermal oil and glycol solution.

Release of a gaseous carbon dioxide-rich intermediate from a carbon dioxide-comprising liquid solution feed 42A is effected. The carbon dioxide-comprising liquid solution feed 42A includes at least a fraction of the carbon dioxide-comprising liquid solution product 42. In some embodiments, the carbon dioxide-comprising liquid solution feed 42A is defined by at least a fraction of the carbon dioxide-comprising liquid solution product. The gaseous carbon dioxide-rich intermediate includes at least a fraction of the dissolved carbon dioxide of the carbon dioxide-comprising liquid solution feed 42A. In some embodiments, for example, carbon dioxide of the gaseous carbon dioxide-rich intermediate is defined by at least a fraction of the dissolved carbon dioxide of the carbon dioxide-comprising liquid solution feed 42A. In this respect, the carbon dioxide of the gaseous carbon dioxide-rich intermediate includes at least a fraction of the supplied exhausted carbon dioxide, and, in some embodiments, is defined by at least a fraction of the supplied exhausted carbon dioxide. Also in this respect, the carbon dioxide of the gaseous carbon dioxide-rich intermediate includes at least a fraction of the produced carbon dioxide, and, in some embodiments, is defined by at least a fraction of the produced carbon dioxide.

In some embodiments, for example, the carbon dioxide-comprising liquid solution feed 42A includes the one or more other materials supplied by the separation process feed material 24 that are solvated (or dissolved) and included within the carbon dioxide-comprising liquid solution product 42, and that are beneficial to the growth of the phototrophic biomass within the reaction zone 10. Examples of such materials include $SO_x$, $NO_x$, and $NH_3$. In this respect, in some embodiments, for example, the effected release of the gaseous carbon dioxide-rich intermediate from a carbon dioxide-comprising liquid solution feed 42A includes release of these one or more other materials.

In some embodiments, for example, the release is effected by effecting a decrease in the solubility of carbon dioxide within the carbon dioxide-comprising liquid solution feed 42A. By effecting the decrease in solubility of the carbon dioxide within the carbon dioxide-comprising liquid solution feed 42A, carbon dioxide, and, in some embodiments, one or more other materials dissolved within the carbon dioxide-comprising liquid solution feed 42A, become released from each of their respective dissolved relationships or associations from within the carbon dioxide-comprising liquid solution feed 42A. In some cases, this release, for each of these materials is characterized as "effervescence" or "coming out of solution".

In some embodiments, for example, the decrease in the solubility of carbon dioxide within the carbon dioxide-comprising liquid solution feed 42A is effected by effecting an increase in the temperature of the carbon dioxide-comprising liquid solution feed 42A. In some embodiments, for example, the decrease in the solubility of carbon dioxide within the carbon dioxide-comprising liquid solution feed 42A is effected by effecting a decrease in the pressure of the carbon dioxide-comprising liquid solution feed 42A.

In some embodiments, for example, the release of the gaseous carbon dioxide-rich intermediate from the carbon dioxide-comprising liquid solution feed 42A effects formation of a carbon dioxide-lean liquid intermediate, such that a carbon dioxide-comprising mixture 54 is provided including the gaseous carbon dioxide-rich intermediate and the carbon dioxide-lean liquid intermediate.

In some embodiments, for example, in parallel with the release of the gaseous carbon dioxide-rich intermediate from the carbon dioxide-comprising liquid solution feed 42A, depletion of the carbon dioxide, and, in some embodiments, of one or more materials, from the carbon dioxide-comprising liquid solution feed 42A is effected, such that formation of a material depleted carbon dioxide-comprising liquid solution feed 42A is effected, wherein the material depleted carbon dioxide-comprising liquid solution feed 42A includes the carbon dioxide-lean liquid intermediate. In some embodiments, for example, the material depleted carbon dioxide-comprising liquid solution product defines the carbon dioxide-lean liquid intermediate.

A gaseous carbon dioxide-rich recovery product 56 is separated from the carbon dioxide-comprising mixture 54. The gaseous carbon dioxide-rich recovery product 56 includes at least a fraction of the gaseous carbon dioxide-rich intermediate, and, in some embodiments, is defined by at least a fraction of the gaseous carbon dioxide-rich intermediate, such that the gaseous carbon dioxide-rich recovery product 56 includes at least a fraction of the supplied exhausted carbon dioxide, and, in this respect, includes at least a fraction of the produced carbon dioxide. In this respect, the carbon dioxide of the gaseous carbon dioxide-rich recovery product 56 includes at least a fraction of the supplied exhausted carbon dioxide, and, in some embodiments, is defined by at least a fraction of the supplied exhausted carbon dioxide. Also in this respect, the carbon dioxide of the gaseous carbon dioxide-rich recovery product 56 includes at least a fraction of the produced carbon dioxide, and, in some embodiments, is defined by at least a fraction of the produced carbon dioxide.

In some embodiments, for example, the gaseous carbon dioxide-rich recovery product 56 includes the one or more other materials supplied by the separation process feed material 24 that are solvated (or dissolved) and then supplied within the carbon dioxide-comprising liquid solution feed 42A, and that are beneficial to the growth of the phototrophic biomass within the reaction zone 10. Examples of such materials include $SO_x$, $NO_x$, and $NH_3$.

In some embodiments, for example, the gaseous carbon dioxide-rich recovery product also includes at least one of $SO_x$ and $NO_x$ In some embodiments, for example, the concentration of carbon dioxide within the carbon dioxide-rich recovery product 56 is at least 90 volume % based on the total volume of the product 56. In some embodiments, for example, the gaseous carbon dioxide-rich recovery product 56 is substantially pure carbon dioxide.

In some embodiments, for example, the separation of the gaseous carbon dioxide-rich recovery product 56 from the carbon dioxide-comprising mixture 54 includes separation by gravity separation. In some embodiments, for example, the separation is effected in the contacting zone.

In some embodiments, for example, the separation of the gaseous carbon dioxide-rich recovery product 56 from the carbon dioxide-comprising mixture 54 effects separation of a carbon dioxide-lean liquid product 58 from the gaseous carbon dioxide-rich recovery product 56. The carbon dioxide-lean liquid product 58 includes at least a fraction of the carbon dioxide-lean liquid intermediate, and, in some embodiments, for example, is defined by at least a fraction of the carbon dioxide-lean liquid intermediate.

In some embodiments, for example, in parallel with the separation of the gaseous carbon dioxide-rich recovery product 56 from the carbon dioxide-comprising mixture 54, depletion of the carbon dioxide, and, in some embodiments, of one or more materials, from the carbon dioxide-comprising mixture 54 is effected, such that separation of a material depleted carbon dioxide-comprising mixture from the gaseous carbon dioxide-rich recovery product 56 is effected, wherein the material depleted carbon dioxide-comprising mixture includes the carbon dioxide-lean liquid product 58. In some embodiments, for example, the material depleted carbon dioxide-comprising mixture is defined by the carbon dioxide-lean liquid product 58.

In some embodiments, for example, the carbon dioxide-lean liquid product 58 includes carbon dioxide, and in some of these embodiments, also includes $SO_x$ and $NO_x$, but, for each of these, in much smaller concentrations than their corresponding concentrations in the carbon dioxide-rich recovery product 56.

The carbon dioxide-rich separation fraction 28 includes at least a fraction of the gaseous carbon dioxide-rich recovery product 56. In some embodiments, for example the carbon dioxide-rich separation fraction 28 is defined by at least a fraction of the gaseous carbon dioxide-rich recovery product 56. In this respect, as a corollary, the carbon dioxide-rich separation fraction 28 includes at least a fraction of the supplied exhausted carbon dioxide, and, in this respect, includes at least a fraction of the produced carbon dioxide. Also in this respect, as a corollary, the carbon dioxide of the carbon dioxide-rich separation 28 includes at least a fraction of the supplied exhausted carbon dioxide, and, in some embodiments, is defined by at least a fraction of the supplied exhausted carbon dioxide. Also in this respect, as a corollary, the carbon dioxide of the carbon dioxide-rich separation 28 includes at least a fraction of the produced carbon dioxide, and, in some embodiments, is defined by at least a fraction of the produced carbon dioxide.

In some embodiments, for example, the carbon dioxide-rich separation fraction 28 includes the one or more other materials supplied by the separation process feed material 24 that are solvated (or dissolved), then supplied within the carbon dioxide-comprising liquid solution feed 42A, and then provided within the gaseous carbon dioxide-rich recovery product 56, and that are beneficial to the growth of the phototrophic biomass within the reaction zone 10. Examples of such materials include $SO_x$, $NO_x$, and $NH_3$.

In some embodiments, for example, the carbon dioxide-comprising liquid solution feed 42A is supplied to a carbon dioxide recovery zone 60, wherein the above-described release of the gaseous carbon dioxide-rich intermediate from the carbon dioxide-comprising liquid solution feed 42A is effected in the carbon dioxide recovery zone 60.

In some embodiments, for example, the temperature within the carbon dioxide recovery zone 60 is higher than the temperature of the contacting zone 34, so as to effect the release of the gaseous carbon dioxide-rich intermediate from the carbon dioxide-comprising liquid solution feed 42A. In this respect, in some embodiments, for example, the temperature within the carbon dioxide recovery zone 60 is higher than the temperature within the contacting zone 34 by at least 15 degrees Celsius. In some embodiments, for example, this temperature difference is at least 20 degrees Celsius. In some embodiments, for example, this temperature difference is at least 25 degrees Celsius. In some embodiments, for example, this temperature difference is at least 30 degrees Celsius. In this respect, in those embodiments, where the operative solvation (or dissolution) agent is an aqueous material, the temperature within the carbon dioxide recovery zone is at least 17 degrees Celsius.

It is understood that the temperature within the carbon dioxide recovery zone 60 is dependent on the temperature within the contacting zone 34, as well as on the composition of the separation fraction 24 to be recovered. The extent of the temperature spread between the carbon dioxide recovery zone 60 and the contacting zone 34 is dictated by the solubility characteristics of the materials within the separation fraction 24 to be recovered. In order to effect the desired solvation (or dissolution) of materials within the contacting zone 34, and then effect the desired release (or effervescence) of those same materials within the carbon dioxide recovery zone 60, for each of these materials, the solubility of the material within the solvent provided in the carbon dioxide recovery zone 60 must be sufficiently lower than the solubility of the same material within the solvent provided in the contacting zone 34 such that meaningful recovery of such material from the separation process feed material 24 is effected.

In some embodiments, for example, the pressure of the carbon dioxide recovery zone 60 is lower than the pressure of the contacting zone 34. This also effects the release of the gaseous carbon dioxide-rich intermediate from the carbon dioxide-comprising liquid solution feed 42A. In some embodiments, for example, a vacuum is generated within the recovery zone so as to effect the release.

In some embodiments, for example, the carbon dioxide-comprising liquid solution feed 42A is supplied to a carbon dioxide recovery zone 60 as a flow. In some embodiments, for example, the flow of the carbon dioxide-comprising liquid solution feed 42A is effected by a prime mover, such as a pump. In some embodiments, for example, flow of the carbon dioxide-comprising liquid solution feed 42A from the contacting zone 34 to the carbon dioxide recovery zone 60 is effected by gravity. In some embodiments, for example, the carbon dioxide-comprising liquid solution feed 42A from the contacting zone 34 to the carbon dioxide recovery zone 60 is effected by a a prime mover, such as a pump, whose suction is disposed in fluid communication with the carbon dioxide recovery zone 60.

In some embodiments, for example, a heat exchanger 64 is disposed in thermal communication with the carbon dioxide recovery zone 60 to effect an increase in the temperature of the carbon dioxide-comprising liquid solution feed 42A, and thereby effect a decrease in solubility of the carbon dioxide within the carbon dioxide-comprising liquid solution feed 42A. In some embodiments, for example, the carbon dioxide recovery zone 60 is disposed in a carbon dioxide recovery tank 66, and the heat exchanger 64 is mounted in thermal communication with the external surface of the carbon dioxide recovery tank 66.

In some embodiments, for example, the separation of the gaseous carbon dioxide-rich recovery product 56 from the carbon dioxide-comprising mixture 54 is effected in the carbon dioxide recovery zone 60.

In some embodiments, for example, the carbon dioxide recovery tank 66 contains a carbon dioxide recovery zone liquid material 68 disposed within the carbon dioxide recovery zone 60, and also includes a headspace 70 disposed above the carbon dioxide recovery zone liquid material for collecting the gaseous carbon dioxide-rich recovery product 56. In some embodiments, for example, the carbon dioxide recovery zone liquid material 68 includes a vertical extent of at least three (3) feet. In some embodiments, for example, the vertical extent is at least ten (10) feet. In some embodiments, for example, this vertical extent is between ten (10) and twenty (20) feet. In some embodiments, for example, sufficient volume of carbon dioxide recovery zone liquid material 68 is provided, and co-operates with a disposition of the outlet for discharging the liquid material 68, such that sufficient residence time is provided within the carbon dioxide recovery zone 60 for effecting the desired release and separation of carbon dioxide from the liquid material 68 prior to discharge of the liquid material 68 from the carbon dioxide recovery zone 60. The carbon dioxide recovery zone liquid material 68 includes the material depleted carbon dioxide-comprising liquid solution product. In some embodiments, for example, the carbon dioxide recovery zone liquid material 68 includes a fraction of the carbon dioxide-comprising liquid solution feed 42A from which carbon dioxide, and, in some embodiments, one or more other materials, have not been separated. In some embodiments, for example, the carbon dioxide-comprising liquid solution feed 42A is supplied to the carbon dioxide recovery zone 60 by introduction into a lower portion of the carbon dioxide recovery zone liquid material 68, and is heated by heat that is thermally communicated to the carbon dioxide recovery zone liquid material 68 from in and around the lower portion of the carbon dioxide recovery zone liquid material 68.

In some embodiments, for example, the gaseous carbon dioxide-rich recovery product 58 is discharged from the carbon dioxide recovery tank 66. In some embodiments, for example, the discharge of the gaseous carbon dioxide-rich recovery product 66 from the headspace 70 of the carbon dioxide recovery tank 66 is effected with a vacuum. In some embodiments, for example, a vacuum generated is such that the pressure within the headspace is between 10 and 14.7 psia, and is also lower than the pressure in the contacting zone 34. In some embodiments, for example, the vacuum is generated by a prime mover or eductor that is fluidly coupled to the headspace for effecting supply of at least a fraction of the gaseous carbon dioxide-rich recovery product 58 to the reaction zone 10 from the carbon dioxide recovery tank 66.

In some embodiments, for example, the carbon dioxide recovery zone liquid material 68 is discharged from the carbon dioxide recovery zone 60. In some embodiments, the carbon dioxide recovery zone liquid material 68 is discharged from the carbon dioxide recovery zone 60 through an outlet of the carbon dioxide recovery tank 66 disposed proximate to the upper level of the carbon dioxide recovery zone liquid material 68 within the carbon dioxide recovery tank 66. In some embodiments, for example, the outlet is vertically displaced from the upper level of liquid material 68 no further than 25% of the vertical extent of the liquid material disposed within the recovery zone 60. In some embodiments, for example, the outlet is vertically displaced from the upper level of liquid material 68 no further than 15% of the vertical extent of the liquid material disposed within the recovery zone 60. In some embodiments, for example, the outlet is vertically displaced from the upper level of liquid material 68 no further than 10% of the vertical extent of the liquid material disposed within the recovery zone 60. Amongst other things, this mitigates against short-circuiting of the recovery zone 60 by the material supplied by the carbon dioxide-comprising liquid solution feed 42A, which would effectively reduce the residence time of this supplied material within the carbon dioxide recovery zone 60, and thereby decreases the proportion of carbon dioxide that undergoes the above-described release from solution and becomes separated from the liquid material 68 before being discharged from the outlet of the tank 66. As well, in some embodiments, for example, the liquid material 68 disposed closer to the upper level is warmer than the liquid material disposed closer to the bottom of the recovery zone 60, and carbon dioxide is less likely to be in solution in the liquid material 68 disposed closer to the upper level relative to the liquid material disposed closer to the bottom of the recovery zone 60, thereby further reinforcing the desirability of having the discharge effected closer to the upper level of the liquid material 68 within the tank 66. In some embodiment, for example, the discharged carbon dioxide recovery zone liquid material 68 is recycled to provide at least a fraction of the operative solvation (or dissolution) agent 30 to the contacting zone 34. In some embodiments, prior to being introduced into the contacting zone 34, the discharged carbon dioxide recovery zone liquid material 68 is cooled so as to effect a reduction in temperature of the discharged carbon dioxide recovery zone liquid material 68 and thereby render it suitable for use as at least a fraction of the operative solvation (or dissolution) agent 30 being supplied to the contacting zone 34. In this respect, in some embodiments, for example. the discharged carbon dioxide recovery zone liquid material 68 is flowed through a chiller 72 for effecting the reduction in temperature.

In some embodiments, for example, when the carbon dioxide recovery tank 66 is of a relatively wider dimension, the disposition of the outlet relative to the upper level of liquid material 68 is not as critical, so long as the carbon dioxide-comprising liquid solution feed 42A is supplied to the carbon dioxide recovery tank 66 through an inlet that is disposed substantially opposite relative to the outlet, as sufficient residence time is more likely to be realized in such a configuration.

In some embodiments, for example, the chiller 72 is thermally coupled to the heat exchanger 64 with a heat transfer loop that is based on a refrigeration circuit (commercially available) that extracts heat from the relatively warmer discharged carbon dioxide recovery zone liquid material 68 flowing through the chiller to reduce its temperature (for example, to three (3) degrees Celsius) to maximize the solubility equilibrium of the soluble gases in the separation process feed material 24. The heat extracted from the discharged carbon dioxide recovery zone liquid material 68 is returned to the carbon dioxide recovery 60, to have the inverse effect and allow the dissolved gases in the carbon dioxide-comprising liquid solution feed 42A to escape into the headspace 70 by increasing the temperature of the carbon dioxide-comprising liquid solution feed 42A, and thereby decreasing the solubility of the gases that have been previously solvated (or dissolved).

At least a fraction of the carbon dioxide-rich product material 26 is supplied to the reaction zone 10 as a carbon dioxide-rich product material supply. The reaction zone feed material 80, being introduced to the reaction zone, includes the carbon dioxide-rich product material supply. In this respect, the reaction zone feed material 80 includes at least a fraction of the carbon dioxide-rich product material 26. In some embodiments, for example, the reaction zone feed material 80 is defined by at least a fraction of the carbon dioxide-rich product material 26. In this respect, as a corollary, the reaction zone feed material includes carbon dioxide of the carbon dioxide-rich product material 26. As such, the reaction zone feed material 80 includes at least a fraction of the supplied exhausted carbon dioxide, and, in this respect, includes at least a fraction of the produced carbon dioxide. As a further corollary, the carbon dioxide of the reaction zone feed material includes at least a fraction of the supplied exhausted carbon dioxide, and, in this respect, includes at least a fraction of the produced carbon dioxide. In some embodiments, for example, the carbon dioxide of this reaction zone feed material 80 is defined by at least a fraction of the supplied exhausted carbon dioxide, and, in this respect, is defined by the produced carbon dioxide.

In some of these embodiments, for example, introduction of the reaction zone feed material 80 to the reaction zone 10 is effected while the gaseous exhaust material 14 is being discharged by the gaseous exhaust material producing process 16.

In some embodiments, for example, the pressure of the carbon dioxide-rich product material supply is increased before being supplied to the reaction zone 10. In some embodiments, for example, the pressure increase is at least partially effected by a prime mover 76. For those embodiments where the carbon dioxide-rich product material supply 26 is disposed within a liquid-comprising material, a suitable prime mover 76 is, for example, a pump. For those embodiments where the carbon dioxide-rich product material supply is disposed within a gaseous material, suitable prime movers 76 include, for example, blowers, compressors, and air pumps. In other embodiments, for example, the pressure increase is effected by a jet pump or eductor.

With respect to such embodiments, where the pressure increase is effected by a jet pump or eductor, in some of these embodiments, for example, the carbon dioxide-rich product material supply is supplied to the jet pump or eductor and pressure energy is transferred to the reaction zone carbon dioxide feed material from another flowing fluid (the "motive fluid flow") using the venturi effect to effect a pressure increase in the carbon dioxide-rich product material supply. In this respect, in some embodiments, for example, and referring to FIG. 3, a motive fluid flow 100 is provided, wherein material of the motive fluid flow 100 includes a motive fluid pressure $P_{M1}$ In this respect also, a lower pressure state reaction zone feed-comprising material 300 is provided including a pressure $P_E$, wherein the lower pressure state reaction zone feed comprising material 300 includes the carbon dioxide-rich product material supply. In some embodiments, the lower pressure state reaction zone feed-comprising material is defined by the carbon dioxide-rich product material supply. $P_{M1}$ of the motive fluid flow is greater than $P_E$ of the lower pressure state reaction zone feed-comprising material. Pressure of the motive fluid flow 100 is reduced from $P_{M1}$ to $P_{M2}$, such that $P_{M2}$ is less than $P_E$, by flowing the motive fluid flow 100 from an upstream fluid passage portion 102 to an intermediate downstream fluid passage portion 104. The intermediate downstream fluid passage portion 104 is characterized by a smaller cross-sectional area relative to the upstream fluid passage portion 102. By flowing the motive fluid flow from the upstream fluid passage portion 102 to the intermediate downstream fluid passage portion 104, static pressure energy is converted to kinetic energy. When the pressure of the motive fluid flow 100 has becomes reduced to $P_{M2}$, fluid communication between the motive fluid flow 100 and the lower pressure state reaction zone feed-comprising material 300 is effected such that the lower pressure state reaction zone feed-comprising material 300 is induced to mix with the motive fluid flow 100 in the intermediate downstream fluid passage portion 104, in response to the pressure differential between the lower pressure state reaction zone feed-comprising material 300 and the motive fluid flow 100, to produce an intermediate reaction zone feed-comprising material 302 which includes the carbon dioxide-rich product material supply. Pressure of the intermediate reaction zone feed-comprising material 302, which includes the carbon dioxide-rich product material supply, is increased to $P_{M3}$, such that the pressure of the carbon dioxide-rich product material supply is also increased to $P_{M3}$. $P_{M3}$ is greater than $P_E$ and is also sufficient to effect supply of the carbon dioxide-rich product material supply to the reaction zone 10 and, upon supply of the carbon dioxide-rich product material supply to the reaction zone 10 as at least a fraction of the reaction zone feed material 80, effect flow of the carbon dioxide-rich product material supply through a vertical extent of reaction mixture within the reaction zone 10 of at least a seventy (70) inches. In some embodiments, for example, $P_{M3}$ is greater than $P_E$ and is also sufficient to effect supply of the carbon dioxide-rich product material supply to the reaction zone 10 and, upon supply of the carbon dioxide-rich product material supply to the reaction zone 10, effect flow of the carbon dioxide-rich product material supply through a vertical extent of reaction mixture within the reaction zone 10 of at least 10 feet. In some embodiments, for example, $P_{M3}$ is greater than $P_E$ and is also sufficient to effect supply of the carbon dioxide-rich product material supply to the reaction zone 10 and, upon supply of the carbon dioxide-rich product material supply to the reaction zone 10, effect flow of the carbon dioxide-rich product material supply through a vertical extent of reaction mixture within the reaction zone 10 of at least 20 feet. In some embodiments, for example, $P_{M3}$ is greater than $P_E$ and is also sufficient to effect supply of the carbon dioxide-rich product material supply to the reaction zone 10 and, upon supply of the carbon dioxide-rich product material supply to the reaction zone 10, effect flow of the carbon dioxide-rich product material supply through a vertical extent of reaction mixture within the reaction zone 10 of at least 30 feet. In any of these embodiments, the pressure increase is designed to overcome the fluid head within the reaction zone 10. The pressure increase is effected by flowing the intermediate reaction zone feed-comprising material 302 from the intermediate downstream fluid passage portion 104 to a "kinetic energy to static pressure energy conversion" downstream fluid passage portion 106. The cross-sectional area of the "kinetic energy to static pressure energy conversion" downstream fluid passage portion 106 is greater than the cross-sectional area of the intermediate downstream fluid passage portion 104, such that kinetic energy of the intermediate reaction zone feed-comprising material 302 disposed in the intermediate downstream fluid passage portion 104 is converted into static pressure energy when the intermediate reaction zone feed-comprising material 302 becomes disposed in the "kinetic energy to static pressure energy conversion" downstream fluid passage portion 106 by virtue of the fact that the intermediate reaction zone feed-comprising material 302 has become flowed to a fluid passage portion with a larger cross-sectional area. In some embodiments, for example, a converging nozzle portion of a fluid passage defines the upstream fluid passage portion 102 and a diverging nozzle portion of the fluid passage defines the "kinetic energy to static pressure energy conversion" downstream fluid passage portion 106, and the intermediate downstream fluid passage portion 104 is disposed intermediate of the converging and diverging nozzle portions. In some embodiments, for example, the combination of the upstream fluid passage portion 102 and the "kinetic energy to static pressure energy conversion" downstream fluid passage portion 106 is defined by a venture nozzle. In some embodiments, for example, the combination of the upstream fluid passage portion 102 and the "kinetic energy to static pressure energy conversion" downstream fluid passage portion 106 is disposed within an eductor or jet pump. In some of these embodiments, for example, the motive fluid flow includes liquid aqueous material and, in this respect, the intermediate reaction zone feed-comprising material 302 includes a combination of liquid and gaseous material, and includes the carbon dioxide-rich product material supply. In this respect, in some embodiments, for example, the intermediate reaction zone feed-comprising material 302 includes a dispersion of a gaseous material within a liquid material, wherein the dispersion of a gaseous material includes the carbon dioxide-rich product material supply. Alternatively, in some of these embodiments, for example, the motive fluid flow is another gaseous flow, such as an air flow, and the intermediate reaction zone feed-comprising material 302 is gaseous. After pressure of the intermediate reaction zone feed-comprising material has been increased to $P_{M3}$, the supply of the carbon dioxide-rich product material by the intermediate reaction zone feed-comprising material 302 to the reaction zone feed material 80 is effected.

The reaction mixture disposed in the reaction zone 10 is exposed to photosynthetically active light radiation so as to effect photosynthesis. The photosynthesis effects growth of the phototrophic biomass.

In some embodiments, for example, the light radiation is characterized by a wavelength of between 400-700 nm. In some embodiments, for example, the light radiation is in the form of natural sunlight. In some embodiments, for example, the light radiation is provided by an artificial light source. In some embodiments, for example, light radiation includes natural sunlight and artificial light.

In some embodiments, for example, the intensity of the provided light is controlled so as to align with the desired growth rate of the phototrophic biomass in the reaction zone 10. In some embodiments, regulation of the intensity of the provided light is based on measurements of the growth rate of the phototrophic biomass in the reaction zone 10. In some embodiments, regulation of the intensity of the provided light is based on the molar rate of supply of carbon dioxide to the reaction zone feed material 80.

In some embodiments, for example, the light is provided at pre-determined wavelengths, depending on the conditions of the reaction zone 10. Having said that, generally, the light is provided in a blue light source to red light source ratio of 1:4. This ratio varies depending on the phototrophic organism being used. As well, this ratio may vary when attempting to simulate daily cycles. For example, to simulate dawn or dusk, more red light is provided, and to simulate mid-day condition, more blue light is provided. Further, this ratio may be varied to simulate artificial recovery cycles by providing more blue light.

It has been found that blue light stimulates algae cells to rebuild internal structures that may become damaged after a period of significant growth, while red light promotes algae growth. Also, it has been found that omitting green light from the spectrum allows algae to continue growing in the reaction zone 10 even beyond what has previously been identified as its "saturation point" in water, so long as sufficient carbon dioxide and, in some embodiments, other nutrients, are supplied.

With respect to artificial light sources, for example, suitable artificial light source 14 include submersible fiber optics, light-emitting diodes, LED strips and fluorescent lights. Any LED strips known in the art can be adapted for use in the process. In the case of the submersible LEDs, the design includes the use of solar powered batteries to supply the electricity. In the case of the submersible LEDs, in some embodiments, for example, energy sources include alternative energy sources, such as wind, photovoltaic cells, fuel cells, etc. to supply electricity to the LEDs.

With respect to those embodiments where the reaction zone 10 is disposed in a photobioreactor 12 which includes a tank, in some of these embodiments, for example, the light energy is provided from a combination of sources, as follows. Natural light source 16 in the form of solar light is captured though solar collectors and filtered with custom mirrors that effect the provision of light of desired wavelengths to the reaction zone 10. The filtered light from the solar collectors is then transmitted through light guides or fiber optic materials into the photobioreactor 12, where it becomes dispersed within the reaction zone 10. In some embodiments, in addition to solar light, the light tubes in the photobioreactor 12 contains high power LED arrays that can provide light at specific wavelengths to either complement solar light, as necessary, or to provide all of the necessary light to the reaction zone 10 during periods of darkness (for example, at night). In some embodiments, with respect to the light guides, for example, a transparent heat transfer medium (such as a glycol solution) is circulated through light guides within the photobioreactor 12 so as to regulate the temperature in the light guides and, in some circumstances, provide for the controlled dissipation of heat from the light guides and into the reaction zone 10. In some embodiments, for example, the LED power requirements can be predicted and, therefore, controlled, based on trends observed with respect to the gaseous exhaust material 18, as these observed trends assist in predicting future growth rate of the phototrophic biomass.

In some embodiments, the exposing of the reaction mixture to photosynthetically active light radiation is effected while the supplying of the reaction zone carbon dioxide feed material is being effected.

In some embodiments, for example, the growth rate of the phototrophic biomass is dictated by the available reaction zone carbon dioxide supply material. In turn, this defines the nutrient, water, and light intensity requirements to maximize phototrophic biomass growth rate. In some embodiments, for example, a controller, e.g. a computer-implemented system, is provided to be used to monitor and control the operation of the various components of the process disclosed herein, including lights, valves, sensors, blowers, fans, dampers, pumps, etc.

Reaction zone product is discharged from the reaction zone. The reaction zone product includes phototrophic biomass-comprising product 58. In some embodiments, for example, the phototrophic biomass-comprising product 58 includes at least a fraction of the contents of the reaction zone 10. In this respect, the discharge of the reaction zone product effects harvesting of the phototrophic biomass 202. In some embodiments, for example, the reaction zone product also includes a reaction zone gaseous effluent product 204 that is discharged within the exhaust 441.

In some embodiments, for example, the harvesting of the phototrophic biomass is effected by discharging the phototrophic biomass 58 from the reaction zone.

In some embodiments, for example, the discharging of the phototrophic biomass 58 from the reaction zone 10 is effected by displacement. In some of these embodiments, for example, the displacement is effected by supply supplemental aqueous material supply 20 to the reaction zone 10. In some of these embodiments, for example, the displacement is an overflow. In some embodiments, for example, the discharging of the phototrophic biomass 58 from the reaction zone 10 is effected by gravity. In some embodiments, for example, the discharging of the phototrophic biomass 58 from the reaction zone 10 is effected by a prime mover that is fluidly coupled to the reaction zone 10.

In some embodiments, for example, the discharge of the phototrophic biomass-comprising product 202 is effected through an outlet extending from the reaction mixture within the reaction zone 10 at a vertical level of the reaction mixture that defines less than 50% of the vertical extent of the reaction mixture within the reaction zone 10. In some embodiments, for example, the outlet extends from the reaction mixture within the reaction zone at a vertical level of the reaction mixture that defines less than 25% of the vertical extent of the reaction mixture within the reaction zone 10. In some embodiments, for example, the outlet extends from the reaction mixture within the reaction zone at a vertical level of the reaction mixture that defines less than 10% of the vertical extent of the reaction mixture within the reaction zone 10. In some embodiments, for example, the outlet extends from the reaction mixture within the reaction zone at a vertical level of the reaction mixture that defines less than 5% of the vertical extent of the reaction mixture within the reaction zone 10. In some embodiments, for example, the outlet extends from the vertically lowermost portion of the reaction mixture within the reaction zone 10. In some of these embodiments, for example, the discharging of the phototrophic biomass-comprising product 202 is effected by gravity. In some of these embodiments, for example, a prime mover, such as a pump, is fluidly coupled to the outlet to effect the discharge of the phototrophic biomass product 202 from the reaction zone 10. In some embodiments, for example, a rotary air lock valve (which also functions as a prime mover) is disposed at the outlet to effect the discharge of the phototrophic biomass product 202 from the reaction zone 10.

In some embodiments, for example, the molar rate of discharge of the product 202 is controlled through the molar rate of supply of supplemental aqueous material supply, which influences the displacement from the photobioreactor 12 of the phototrophic biomass-comprising product 202 from an outlet of the photobioreactor 12. For example, an overflow of an upper portion of phototrophic biomass suspension in the reaction zone 10 from the photobioreactor 12 (for example, the phototrophic biomass is discharged through an overflow port of the photobioreactor 12) is effected by this displacement to provide the phototrophic biomass-comprising product 202. In some embodiments, for example, the discharging of the product 202 is controlled with a prime mover (such as a pump) fluidly coupled to an outlet of the photobioreactor 12.

The phototrophic biomass-comprising product 202 includes water. In some embodiments, for example, the phototrophic biomass-comprising product 202 is supplied to a separator system for effecting removal of at least a fraction of the water from the phototrophic biomass-comprising product 202 to effect production of an intermediate concentrated phototrophic biomass-comprising product (eg. 208) and a recovered aqueous material 210 (generally, water). In some embodiments, the recovered aqueous material 210 re-used by the process.

In some embodiments, for example, the separator system includes a settling column 212, a decanter 214, and a dryer 50.

In some embodiments, for example, the discharged phototrophic biomass-comprising product is supplied to the settling column 212 under a motive force, such as that supplied by a pump. In some embodiments, for example, flocculant 216 is added so as to facilitate settling of the phototrophic biomass within the settling column 212. In some embodiments, for example, the molar rate of supply of flocculant to the phototrophic biomass-comprising product is modulated based on the molar rate of supply of the phototrophic biomass of the phototrophic biomass-comprising product 202 (which, for example, can be determined by sensing molar concentration of phototrophic biomass within the phototrophic biomass-comprising product 202 in combination with the detection of the molar rate of flow of the phototrophic biomass-comprising product 202 being supplied to the settling column 212) to the settling column 212. In some embodiments, aqueous material 201, which has condensed from the heat exchanger 46, as well as the aqueous material 2141 which has been separated from the decanter 214 (see below), is also supplied to the settling column 212 so as to effect their re-use as the supplemental aqueous material supply 20. In some embodiments, for example, liquid level is controlled within the settling column so as to provide sufficient residence time to effect the desired settling of a phototrophic biomass-rich first intermediate product 208. In this respect, in some embodiments, for example, upon determination that a detected liquid level in the settling column 201 is below a predetermined minimum liquid level, water from a municipal water supply is supplied to the settling column to effect an increase to the liquid level, such as by effecting opening of a valve 213. Separation of the phototrophic biomass-rich first intermediate product 208 from an aqueous liquid overhead product 210 is effected by gravity settling in the settling column. In some embodiments, for example, the aqueous liquid overhead product 210 is returned to the photobioreactor 12 as the supplemental aqueous material supply 20 for re-use. In some embodiments, for example, the supplemental nutrient supply is added to the supplemental aqueous material supply 20 prior to supply to the photobioreactor. In some embodiments, for example, the molar rate of supply of the supplemental aqueous material supply 20 to the photobioreactor 12 is modulated based on a detected molar rate of flow of the carbon dioxide-rich product material 26 to the reaction zone 10.

In some embodiments, for example, a level sensor is provided to detect the level of the reaction mixture within the reaction zone 10, and transmit a signal representative of the detected level to a controller. The controller compares the received signal to a predetermined level value. If the received signal is less than the predetermined level value, the controller responds by effecting initiation of supply, or an increase to the molar rate of supply, of the supplemental aqueous material supply 20 to the reaction zone 10, such as by opening (in the case of initiation of supply), or increasing the opening (in the case of increasing the molar rate of supply), of a valve configured to interfere with the supply of the supplemental aqueous material supply 20 to the reaction zone 10. If the received signal is greater than the predetermined level value, the controller responds by effecting a decrease to the molar rate of supply, or termination of supply, of the supplemental aqueous material supply 20 to the reaction zone 10, such as by decreasing the opening of (in the case of decreasing the molar rate of supply), or closing the valve (in the case of terminating the supply) that is configured to interfere with the supply of the supplemental aqueous material supply 20 to the reaction zone 10. In some embodiments, for example, by regulating the supplying of the supplemental aqueous material supply 20 to the reaction zone 10 so as to effect the maintaining of a desired level within the reaction zone 10, make-up water is supplied to the reaction zone 10 to replace water that is discharged with the phototrophic biomass-comprising product 202 with a view to maintaining steady state conditions within the reaction zone 10.

In some embodiments, for example, while growth of the phototrophic biomass is being effected within the reaction mixture disposed within the reaction zone 10 and exposed to the photosynthetically active light radiation, discharge of the phototrophic biomass from the reaction zone 10 is effected at a molar rate of discharge that is equivalent to, or substantially equivalent to, a predetermined molar rate of growth of phototrophic biomass within the reaction mixture which is disposed within the reaction zone 10 and is being exposed to the photosynthetically active light radiation. The growth of the phototrophic biomass includes growth effected by photosynthesis. In some embodiments, for example, the predetermined molar rate of growth of phototrophic biomass is at least 90% of the maximum molar rate of growth of phototrophic biomass within the reaction mixture which is disposed within the reaction zone 10 and is being exposed to the photosynthetically active light radiation. In some embodiments, for example, the predetermined molar rate of growth of phototrophic biomass within the reaction zone 10 is at least 95% of the maximum molar rate of growth of phototrophic biomass within the reaction mixture which is disposed within the reaction zone 10 and is being exposed to the photosynthetically active light radiation. In some embodiments, for example, the predetermined molar rate of growth of phototrophic biomass is at least 99% of the maximum molar rate of growth of phototrophic biomass within the reaction mixture which is disposed within the reaction zone 10 and is being exposed to the photosynthetically active light radiation. In some embodiments, for example, the predetermined molar rate of growth of phototrophic biomass is equivalent to the maximum molar rate of growth of phototrophic biomass within the reaction mixture which is disposed within the reaction zone 10 and is being exposed to the photosynthetically active light radiation. In some embodiments, for example, the discharging of the phototrophic biomass 58 from the reaction zone 10 is effected by displacement. In some of these embodiments, for example, the displacement is effected by supplying supplemental aqueous material supply 20 to the reaction zone 10. In some of these embodiments, for example, the displacement is an overflow. In some embodiments, for example, the discharging of the phototrophic biomass 58 from the reaction zone 10 is effected by gravity. In some embodiments, for example, the discharging of the phototrophic biomass 58 from the reaction zone 10 is effected by a prime mover that is fluidly coupled to the reaction zone 10.

In some embodiments, for example, while growth of the phototrophic biomass is being effected within the reaction mixture disposed within the reaction zone 10 and exposed to the photosynthetically active light radiation, the molar rate of discharge of the phototrophic biomass from the reaction zone 10 is modulated in response to detection of a difference between a phototrophic biomass growth indicator, detected from within the reaction zone 10, and a predetermined phototrophic biomass growth indicator value. The predetermined phototrophic biomass growth indicator value is correlated with a predetermined molar rate of growth of phototrophic biomass within the reaction mixture which is disposed within the reaction zone 10 and is being exposed to the photosynthetically active light radiation. In some embodiments, for example, the predetermined molar rate of growth of phototrophic biomass is based on the maximum molar rate of growth of phototrophic biomass within the reaction mixture which is disposed within the reaction zone 10 and is being exposed to the photosynthetically active light radiation. In some embodiments, for example, the predetermined molar rate of growth of phototrophic biomass is at least 90% of the maximum molar rate of growth of phototrophic biomass within the reaction mixture which is disposed within the reaction zone 10 and is being exposed to the photosynthetically active light radiation. In some embodiments, for example, the predetermined molar rate of growth of phototrophic biomass is at least 95% of the maximum molar rate of growth of phototrophic biomass within the reaction mixture which is disposed within the reaction zone 10 and is being exposed to the photosynthetically active light radiation. In some embodiments, for example, the predetermined molar rate of growth of phototrophic biomass within the reaction mixture is at least 99% of the maximum molar rate of growth of phototrophic biomass within the reaction mixture which is disposed within the reaction zone 10 and is being exposed to the photosynthetically active light radiation. In some embodiments, for example, the predetermined molar rate of growth of phototrophic biomass is equivalent to the maximum molar rate of growth of phototrophic biomass within the reaction mixture which is disposed within the reaction zone 10 and is being exposed to the photosynthetically active light radiation. In some embodiments, for example, the phototrophic biomass growth indicator is a molar concentration of phototrophic biomass. In some embodiments, for example, the predetermined molar rate of growth of phototrophic biomass, with which the predetermined phototrophic biomass growth indicator value is correlated, is based upon a rate of increase in molar concentration of phototrophic biomass within the reaction zone 10 effected by growth of the phototrophic biomass within the reaction mixture which is disposed within the reaction zone 10 and is being exposed to the photosynthetically active light radiation.

In some embodiments, for example, while the modulating of the molar rate of discharge of the phototrophic biomass from the reaction zone 10 is being effected, the volume of the reaction mixture disposed within the reaction zone is maintained constant or substantially constant for a time period of at least one (1) hour. In some embodiments, for example, the time period is at least six (6) hours. In some embodiments, for example, the time period is at least 24 hours. In some embodiments, for example, the time period is at least seven (7) days. In some embodiments, for example, while the modulating is being effected, the volume of the reaction mixture disposed within the reaction zone is maintained constant or substantially constant for the a period of time such that the predetermined phototrophic biomass growth indicator value, as well as the predetermined molar rate of growth of phototrophic biomass, is maintained constant or substantially constant during this period, with a view to optimizing economic efficiency of the process.

In some embodiments, for example, while the modulating of the molar rate of discharge of the phototrophic biomass from the reaction zone 10 is being effected, the process further includes modulating the molar rate of supply of the supplemental nutrient supply to the reaction zone in response to the detection of a difference between a detected molar concentration of one or more nutrients (eg. $NO_3$) within the reaction zone 10 and a corresponding predetermined target molar concentration value. In some embodiments, for example, the molar rate of supply of the supplemental nutrient supply to the reaction zone 10 is modulated in response to a detected change in the molar rate of supply of the carbon dioxide-rich product material 26 to the reaction zone 10.

In some embodiments, for example, while the modulating of the molar rate of discharge of the phototrophic biomass from the reaction zone 10 is being effected, the process further includes modulating the molar rate of supply of the carbon dioxide-rich product material 26 to the reaction zone 10 based on at least one carbon dioxide processing capacity indicator. In some embodiments, for example, the detection of at least one of the at least one carbon dioxide processing capacity indicator is effected in the reaction zone 10. The carbon dioxide processing capacity indicator which is detected is any characteristic that is representative of the capacity of the reaction zone 10 for receiving carbon dioxide and having at least a fraction of the received carbon dioxide converted in a photosynthesis reaction effected by phototrophic biomass disposed within the reaction zone. In some embodiments, for example, the carbon dioxide processing capacity indicator is a pH within the reaction zone 10. In some embodiments, for example, the carbon dioxide processing capacity indicator is a phototrophic biomass molar concentration within the reaction zone 10.

In some embodiments, for example, while the modulating of the molar rate of discharge of the phototrophic biomass from the reaction zone 10 is being effected, the process further includes modulating the intensity of the photosynthetically active light radiation to which the reaction mixture is exposed to, in response to a detected change in the molar rate at which the carbon dioxide-rich product material 26 is being supplied to the reaction zone 10.

In some embodiments, for example, and as described above, the discharge of the phototrophic biomass from the reaction zone 10 is effected by a prime mover, such as a pump. In this respect, in some embodiments, for example, the modulating of the molar rate of discharge of the phototrophic biomass from the reaction zone includes:

(i) modulating the power supplied to the prime mover effecting the discharge of the phototrophic biomass from the reaction zone 10 in response to detection of a difference between a detected phototrophic biomass growth indicator, within the reaction mixture disposed within the reaction zone, and a predetermined phototrophic biomass growth indicator value, wherein the predetermined phototrophic biomass growth indicator target value is correlated with a predetermined molar rate of growth of phototrophic biomass within the reaction mixture which is disposed within the reaction zone 10 and is being exposed to the photosynthetically active light radiation, and;

(ii) while the modulating of the power supplied to the prime mover is being effected, modulating the molar rate of supply of the supplemental aqueous material supply 20 to the reaction zone 10 in response to detection of a difference between a detected indication of volume of reaction mixture within the reaction zone and a predetermined reaction mixture volume indication value, wherein the predetermined reaction mixture volume indication value is representative of a volume of reaction mixture within the reaction zone 10 within which growth of the phototrophic biomass is effected within the reaction mixture at the predetermined molar rate of growth of phototrophic biomass while the phototrophic biomass growth indicator, within the reaction mixture, is disposed at the predetermined phototrophic biomass growth indicator target value.

In some of these embodiments, for example, the predetermined molar rate of growth of the phototrophic biomass is based upon the maximum molar rate of growth of the phototrophic biomass within the reaction mixture which is disposed within the reaction zone 10 and is being exposed to the photosynthetically active light radiation, as described above.

In some embodiments, for example, the phototrophic biomass growth indicator is a molar concentration of phototrophic biomass.

In some embodiments, for example, the indication of volume of reaction mixture within the reaction zone 10 (or, simply, the "reaction mixture volume indication") is an upper liquid level of the reaction mixture within the reaction zone 10. In some embodiments, for example, this upper liquid level is detected with a level sensor, as described above.

The phototrophic biomass-rich first intermediate product 208 is supplied to the decanter 214 to further effect dewatering of the phototrophic biomass and effect separation from the phototrophic biomass-rich first intermediate product 208 of a phototrophic biomass-rich second intermediate product 218 and aqueous product 2181. In some embodiments, for example, the supply of the phototrophic biomass-rich first intermediate product 208 to the decanter 214 is modulated based on the detected concentration of phototrophic biomass within the phototrophic biomass-rich first intermediate product 208. In such embodiments, the phototrophic biomass-rich first intermediate product 208 is supplied to the decanter 214 when the concentration of phototrophic biomass within the phototrophic biomass-rich first intermediate product 208 is above a predetermined concentration. In some embodiments, for example, the supply of the product 208 to the decanter 214 is controlled by a valve 215 that responds to a signal from a controller upon the determination of a deviation of the detected phototrophic biomass concentration within the phototrophic biomass-rich first intermediate product from a predetermined value. In some embodiments, for example, the motor speed of the decanter is controlled by a variable frequency drive, also in response to a signal from a controller upon the determination of a deviation of the detected phototrophic biomass concentration within the phototrophic biomass-rich first intermediate product from a predetermined value. The decanter 214 effects separation of the aqueous product 2181 and the phototrophic biomass-rich second intermediate product 218 from the phototrophic biomass-rich first intermediate product 214. The aqueous product 2181 is supplied to the settling column 212. The phototrophic biomass-rich second intermediate product 218 is discharged from the decanter 214 and supplied to the dryer 50 which supplies heat to the phototrophic biomass-rich second intermediate product 218 to effect evaporation of at least a fraction of the water of the phototrophic biomass-rich second intermediate product 218, and thereby effect production of a final phototrophic biomass-comprising product. As discussed above, in some embodiments, the heat supplied to the intermediate concentrated phototrophic biomass-comprising product 218 is provided by a heat transfer medium which has been used to effect the cooling of the supplied exhaust gas prior to supply of the supplied exhaust gas to the contacting zone. By effecting such cooling, heat is transferred from the supplied exhaust gas to the heat transfer medium, thereby raising the temperature of the heat transfer medium. In such embodiments, the heat requirement to effect evaporation of water from the phototrophic biomass-rich second intermediate product is not significant, thereby rendering it feasible to use the heated heat transfer medium as a source of heat to effect the drying of the phototrophic biomass-rich second intermediate product. After heating the phototrophic biomass-rich second intermediate product, the heat transfer medium, having lost some energy and becoming disposed at a lower temperature, is recirculated to the heat exchanger to effect cooling of the supplied exhaust gas. The heating requirements of the dryer 50 is based upon the rate of supply of the phototrophic biomass-rich second intermediate product to the dryer 50. Cooling requirements (of the heat exchanger) and heating requirements (of the dryer 50) are adjusted by the controller to balance the two operations by monitoring flowrates and temperatures of each of the supplied exhaust gas and the rate of production of the product 202 through discharging of the product 202 from the photobioreactor 12.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

The invention claimed is:

1. A process for growing a phototrophic biomass in a reaction zone comprising:
producing carbon dioxide supply-comprising gaseous material feed with a gaseous exhaust material producing process;
effecting separation, from the carbon dioxide supply-comprising gaseous material feed, of a gaseous carbon dioxide-rich product material, wherein the carbon dioxide concentration of the carbon dioxide-rich product material is greater than the carbon dioxide concentration of the carbon dioxide supply-comprising gaseous material feed, wherein the effecting separation comprises:
contacting the carbon dioxide supply-comprising gaseous material feed with a dissolution agent, within a contacting zone disposed at a pressure of between 10 psia and 25 psia and at a temperature of between two (2) degrees Celsius and four (4) degrees Celsius, such that dissolution of at least a fraction of the carbon dioxide supply-comprising gaseous material feed with the dissolution agent is effected so as to effect production of a carbon dioxide-comprising liquid solution product comprising dissolved carbon dioxide; and
indirectly heating the carbon dioxide-comprising liquid solution product with a heat exchanger with effect that the gaseous carbon dioxide-rich product material and a carbon dioxide-depleted aqueous liquid material are produced;
separating the gaseous carbon dioxide-rich product material from the carbon dioxide-depleted aqueous liquid; and
supplying at least a fraction of the gaseous carbon dioxide-rich product material to the reaction zone so as to effect growth of the phototrophic biomass by photosynthesis in the reaction zone,
wherein the dissolution agent includes water and the cooled fraction of carbon dioxide-depleted aqueous liquid.

2. The process of claim 1, wherein the carbon dioxide supply-comprising gaseous material feed comprises at least one relatively less soluble material, wherein, relative to carbon dioxide, each one of the at least one relatively less soluble material is less soluble within the operative dissolution agent, when the operative dissolution agent is disposed within the contacting zone.

3. The process of claim 1, wherein the process further comprises:
harvesting a phototrophic biomass-comprising product from the reaction zone, wherein the phototrophic biomass-comprising product comprises the phototrophic biomass and an aqueous liquid;
effecting separation of at least a fraction of the aqueous liquid from the phototrophic biomass-comprising product to produce a separated aqueous liquid; and
recycling the separated aqueous liquid to the contacting zone.

4. A process for growing a phototrophic biomass in a reaction zone comprising:
producing carbon dioxide supply-comprising gaseous material feed with a gaseous exhaust material producing process;
effecting separation, from the carbon dioxide supply-comprising gaseous material feed, of a gaseous carbon dioxide-rich product material, wherein the carbon dioxide concentration of the carbon dioxide-rich product material is greater than the carbon dioxide concentration of the carbon dioxide supply-comprising gaseous material feed, wherein the effecting separation comprises:
contacting the carbon dioxide supply-comprising gaseous material feed with a dissolution agent within a contacting zone, such that dissolution of at least a fraction of the carbon dioxide supply-comprising gaseous material feed with the dissolution agent is effected so as to effect production of a carbon dioxide-comprising liquid solution product comprising dissolved carbon dioxide; and
indirectly heating the carbon dioxide-comprising liquid solution product with a heat exchanger with effect that the gaseous carbon dioxide-rich product material and a carbon dioxide-depleted aqueous liquid material are produced;
separating the gaseous carbon dioxide-rich product material from the carbon dioxide-depleted aqueous liquid;
supplying at least a fraction of the gaseous carbon dioxide-rich product material to the reaction zone so as to effect growth of the phototrophic biomass by photosynthesis in the reaction zone;

harvesting a phototrophic biomass-comprising product from the reaction zone, wherein the phototrophic biomass-comprising product comprises the phototrophic biomass and an aqueous liquid;

effecting separation of at least a fraction of the aqueous liquid from the phototrophic biomass-comprising product to produce a separated aqueous liquid; and recycling the separated aqueous liquid to the contacting zone, wherein the dissolution agent includes the cooled fraction of the carbon dioxide-depleted aqueous liquid.

5. The process of claim 1, wherein the process further comprises: cooling at least a fraction of the carbon dioxide-depleted aqueous liquid with a chiller that is thermally coupled to the heat exchanger.

6. The process of claim 5, wherein the cooling is via a refrigeration cycle.

7. The process of claim 1, wherein the reaction zone is disposed at atmospheric pressure.

8. The process of claim 4, wherein the process further comprises: cooling at least a fraction of the carbon dioxide-depleted aqueous liquid with a chiller that is thermally coupled to the heat exchanger.

9. The process of claim 8, wherein the cooling is via a refrigeration cycle.

10. The process of claim 4, wherein the reaction zone is disposed at atmospheric pressure.

* * * * *